(12) United States Patent
Locke et al.

(10) Patent No.: US 12,268,835 B2
(45) Date of Patent: Apr. 8, 2025

(54) APPARATUS, SYSTEM, AND METHOD FOR THERAPY SYSTEM COMPONENTS EMPLOYING LIGHT SWITCHABLE ADHESIVES

(71) Applicant: Solventum Intellectual Properties Company, Maplewood, MN (US)

(72) Inventors: Christopher Brian Locke, Bournemouth (GB); Timothy Mark Robinson, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 943 days.

(21) Appl. No.: 17/419,098

(22) PCT Filed: Jan. 7, 2020

(86) PCT No.: PCT/US2020/012467
§ 371 (c)(1),
(2) Date: Jun. 28, 2021

(87) PCT Pub. No.: WO2020/146306
PCT Pub. Date: Jul. 16, 2020

(65) Prior Publication Data
US 2022/0072294 A1    Mar. 10, 2022

Related U.S. Application Data

(60) Provisional application No. 62/790,196, filed on Jan. 9, 2019.

(51) Int. Cl.
*A61M 39/10* (2006.01)
*A61M 5/142* (2006.01)
*C09J 9/00* (2006.01)

(52) U.S. Cl.
CPC ............ *A61M 39/10* (2013.01); *A61M 5/142* (2013.01); *C09J 9/00* (2013.01)

(58) Field of Classification Search
CPC .... A61M 39/10; A61M 5/142; A61M 5/1413; A61M 5/14248; A61M 1/90; A61M 1/912; A61M 1/92; C09J 9/00; A61B 5/6833

(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 650575 B2 | 3/1986 |
| AU | 745271 B2 | 3/2002 |

(Continued)

OTHER PUBLICATIONS

International Search Report for PCT International Application PCT/GB95/01983; Nov. 23, 1995.

(Continued)

*Primary Examiner* — Catharine L Anderson
*Assistant Examiner* — Quynh Dao Le

(57) ABSTRACT

This disclosure describes devices, systems, and methods related to a connection point of a therapy system which includes light switchable adhesive and is configured to be switched by light provided by and/or via one or more components of the therapy system. An example of a connection point is an interface between two tubes of therapy system. An example of light provided to the exemplary connection point is light provided to one of the two tubes such that the light travels to the connection point, via at least the one tube, to switch the light switchable adhesive.

3 Claims, 8 Drawing Sheets

(58) Field of Classification Search
USPC .................. 604/289, 180, 305, 174, 307
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,610,762 B1* | 8/2003 | Webster | C08F 8/32 522/119 |
| 6,814,079 B2 | 11/2004 | Teaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0019127 A1* | 1/2004 | Yamamoto | C08G 18/6254 522/39 |
| 2006/0225832 A1 | 10/2006 | Saidman et al. | |
| 2007/0129707 A1* | 6/2007 | Blott | A61F 13/05 604/308 |
| 2009/0312727 A1* | 12/2009 | Heaton | A61M 1/966 604/319 |
| 2014/0155791 A1* | 6/2014 | Robinson | A61H 9/0057 601/7 |
| 2015/0216733 A1* | 8/2015 | Allen | A61F 13/5376 604/319 |
| 2017/0051189 A1* | 2/2017 | Tunius | A61L 31/041 |
| 2019/0290496 A1* | 9/2019 | Brownhill | A61F 13/05 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2 371 920 A1 | 10/2011 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

(56) References Cited

FOREIGN PATENT DOCUMENTS

| WO | WO-00/61692 A1 | 10/2000 |
| WO | WO-2011/086505 A1 | 7/2011 |
| WO | WO-2019/083869 A1 | 5/2019 |

OTHER PUBLICATIONS

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Chariker, Mark E., M.D., et al; "Effective Management of incisional and cutaneous fistulae with closed suction wound drainage"; Contemporary Surgery, vol. 34, Jun. 1989, pp. 59-63.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A.C. ® Therapy Clinical Guidelines: A Reference Source for Clinicians; Jul. 2007.

International Search Report & Written Opinion on International Patent Application No. PCT/US2020/012467 dated Apr. 7, 2020 (13 pages).

* cited by examiner

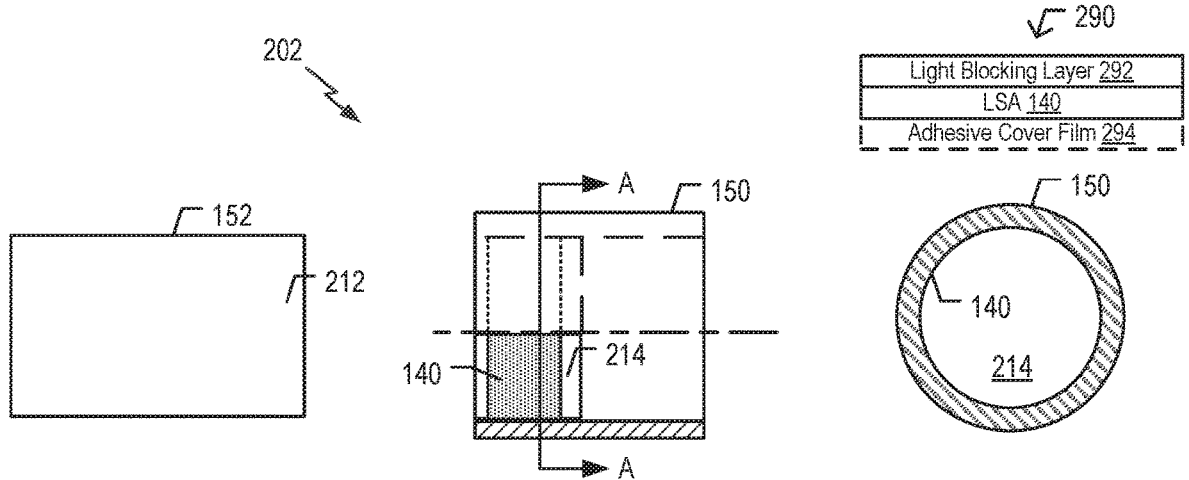
FIG. 2A
FIG. 2B
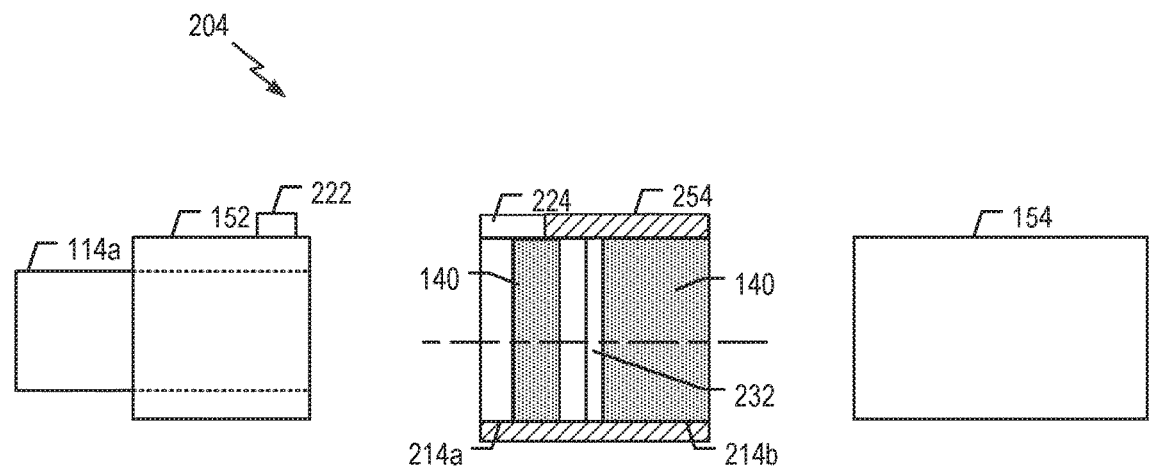
FIG. 2C
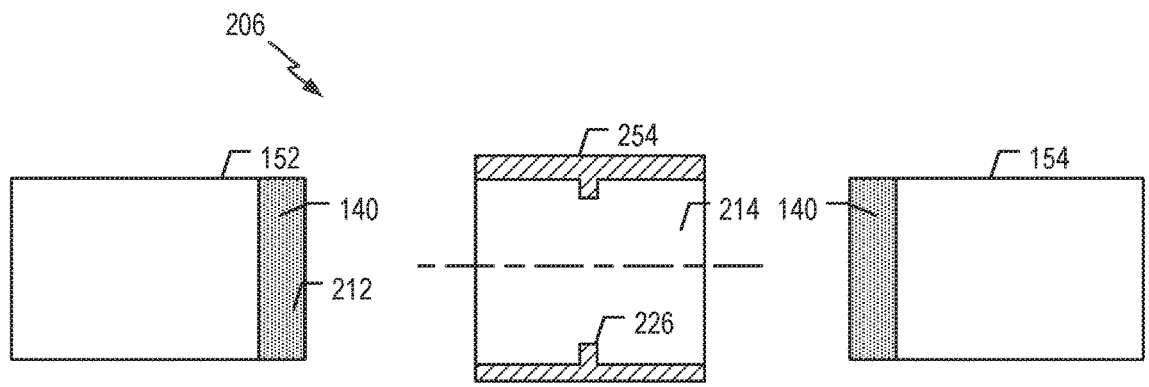
FIG. 2D

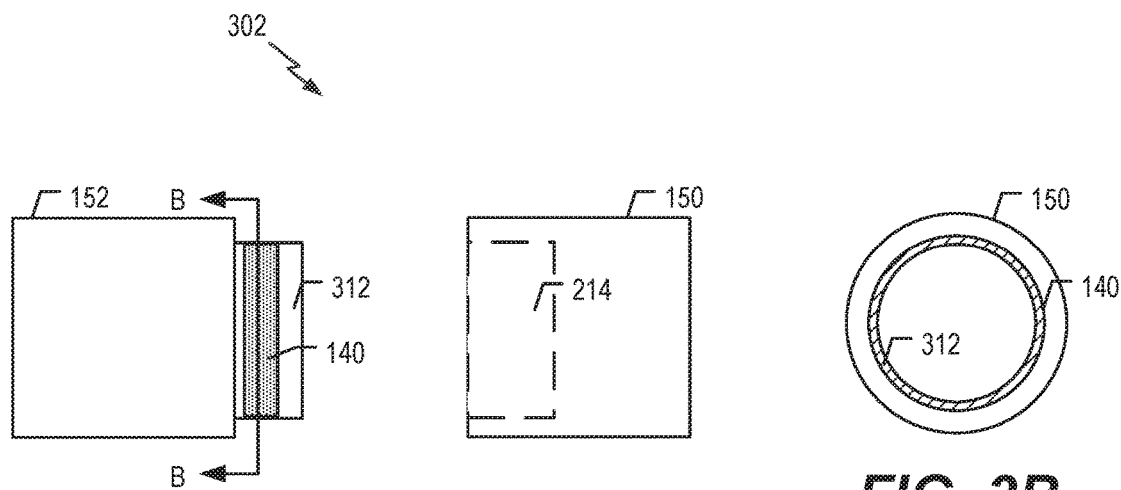
FIG. 3A
FIG. 3B
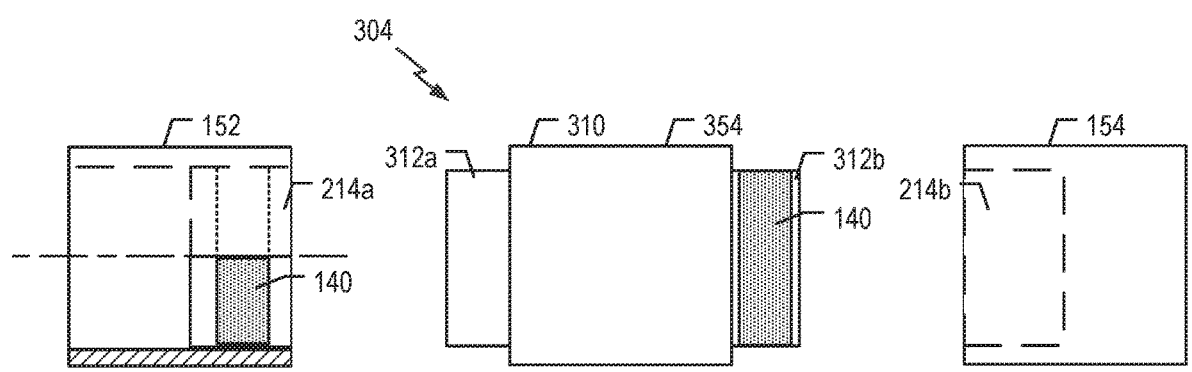
FIG. 3C
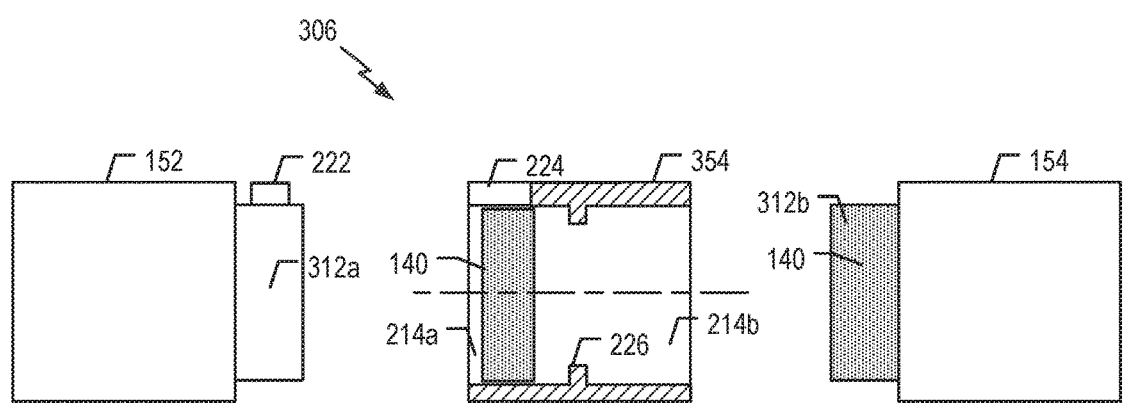
FIG. 3D

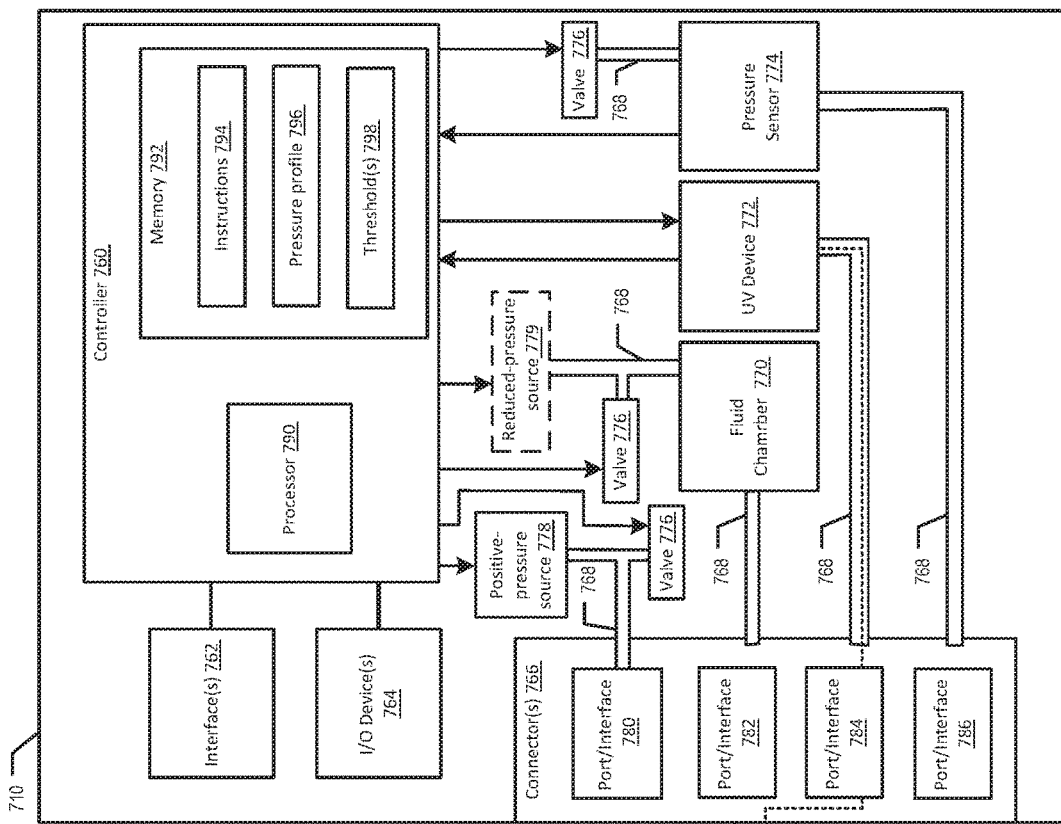
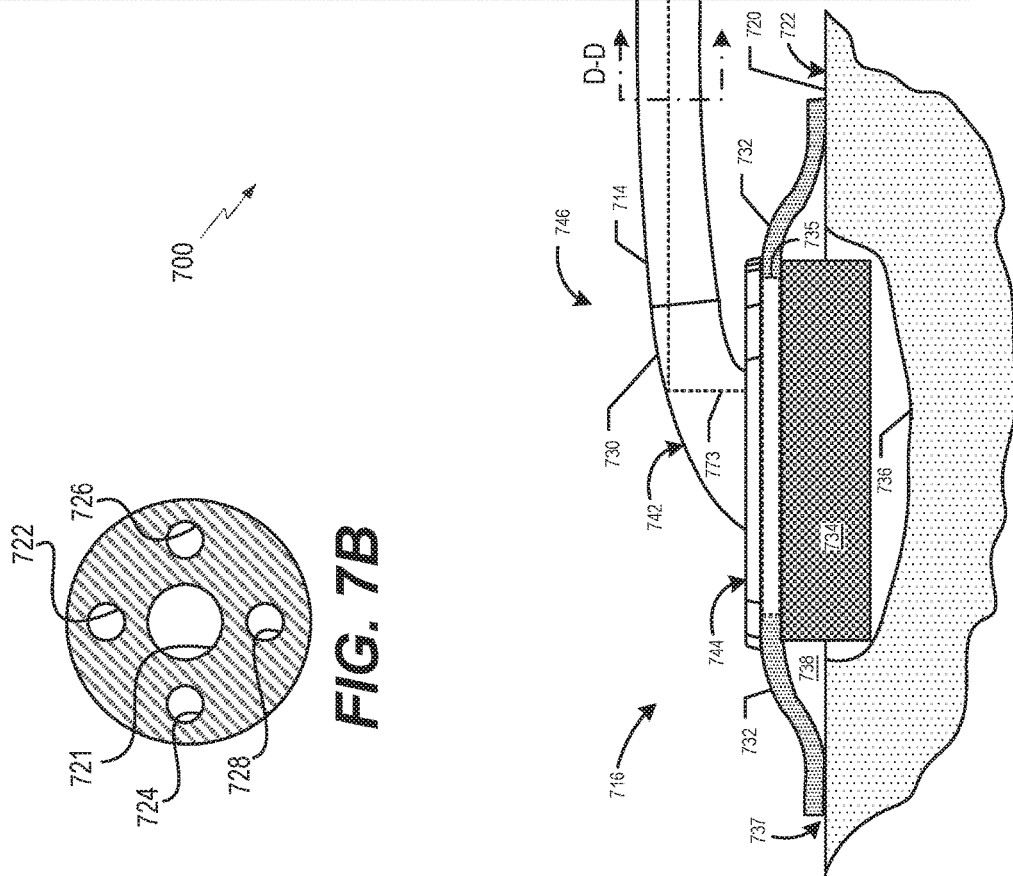
FIG. 7A
FIG. 7B

APPARATUS, SYSTEM, AND METHOD FOR THERAPY SYSTEM COMPONENTS EMPLOYING LIGHT SWITCHABLE ADHESIVES

CROSS-REFERENCE TO RELATED APPLICATIONS

This application is a US national phase application under 35 USC § 371 of International Application No. PCT/US2020/012467 filed on Jan. 7, 2020, which claims the benefit of priority to U.S. Provisional Application No. 62/790,196, entitled "Apparatus, System, and Method for Therapy System Components Employing Light Switchable Adhesives" filed on Jan. 9, 2019, the contents of which are both incorporated into the present application in their entireties.

TECHNICAL FIELD

Aspects of the present disclosure relate generally to switchable adhesives, and more specifically, but not by way of limitation, to lumens and connectors including light switchable adhesive.

BACKGROUND

Therapy systems often use single-use disposable components because they are sterile. Reusing components, especially components designed to be used once and disposed, increases contamination of the therapy system and complications, such as infections, increased recovery times, etc. A challenge with all single-use disposable components (e.g., tube-sets, canisters, etc.) is that making the single-use components easier to use (e.g., connect and disconnect) often makes the single-use components easier to reuse. For example, in-line connectors often have a mechanical interlock that is robust enough so that the connector can mate with multiple different types of tubes/connectors and meet one or more design specifications. Often times, such robust mechanical interlock designs will enable the connectors to be durable enough to be used multiple times even though the connector and/or the system may be designed to be used once, such as to prevent contamination or infection. Similarly, canisters and therapy devices which can be disconnected and reconnected to other components of a therapy system also pose contamination and infection risks from reuse.

As another example of a challenge with single-use disposable components, therapy system components, (e.g., tube sets and/or canisters) may employ pressure sensitive adhesives for connections that are strong enough to create fluid tight seals (e.g., non-permeable seals) and prevent accidental disconnections. However, such adhesives may be durable enough and/or have sufficient rebonding capability (e.g., high tackiness, peel strength, or both) to be usable multiple times before the adhesives lose sufficient bonding capability and no longer functions properly as an adhesive. Additionally, such pressure sensitive adhesives may be difficult for certain people to remove. For example, children, elderly, and less-abled people may find that the peel strength sufficient to seal the components and form an operable connection to be used in therapy system is difficult, painful, and/or harmful to remove.

Light switchable adhesives have been included in wound dressings and bandages. However, such conventional light switchable adhesive require a separate device to switch the light switchable adhesive, require protective elements to shield the light switchable adhesive from ambient light, and/or prohibit a patient being exposed to sunlight during use of the light switchable adhesive.

Thus, conventional therapy systems suffer from multiple challenges. For example, disposable components that are easy to use are often easy to reuse, which increases infection and contamination risks. Therapy systems which utilize pressure sensitive adhesives can be difficult for children, elderly, and less-abled people to disconnect. Additionally, bandages that employ light switchable adhesives employ additional components and/or limit or restrict patient mobility.

SUMMARY

The present disclosure describes devices, systems, and methods related to a light switchable adhesive based connection point (e.g., an interface) in a therapy system. An exemplary therapy system (e.g., a modular therapy system or a therapy system kit) may include one or more connection points (e.g., interfaces) of the therapy system, such as connections points between a therapy device and a canister, between the canister and a set of tubes, within the set of tubes, between the set of tubes and a dressing, and between the dressing and the patient. A light switchable adhesive connection point includes or corresponds to an interface between two components, two subcomponents, or a component and a patient that employs a light switchable adhesive to form a bond between the components and/or the patient. A light switchable adhesive can be employed in various ways, as described herein, to form the connection point of the therapy system. Additionally, the light switchable adhesives of the connection points can be activated, i.e., switched or transitioned, in various ways, described herein, to facilitate disconnection of the connection points. One particular way of activating the light switchable adhesives is by incorporating a light source into the therapy system and using one or more components of the therapy system to transport (e.g., propagate) light from the light source to one or more connections points of the therapy system. Thus, the therapy system can generate light and the components thereof may enable delivery of the light to components and connection points that are remote from the light source.

Light switchable adhesives (often referred to as switched or light switched adhesives) are pressure sensitive adhesives that are "switchable" from a tacky state (e.g., a first state) to a non-tacky or low-tack state (e.g., a second state) in which the light switchable adhesive has a reduced peel strength relative to the peel strength of the first state of the light switchable adhesive before switching. To illustrate, light, such as ultraviolet light, triggers (e.g., activates) cross linking in the light switchable adhesive which effectively decreases the bond (and peel strength) of the light switchable adhesive and allows two components to decouple with reduced force. The cross linking in the light switchable adhesive also prevents the light switchable adhesive and the components from being reconnected as well. To illustrate, once the light switchable adhesive is switched from the first state to the second state by crosslinking it becomes brittle and fragile, and the light switchable adhesive cannot be "uncrosslinked" or "unswitched." Thus, the components cannot be reused and/or resecured together with the light switchable adhesive.

The light switchable adhesive based connections points described herein enable secure strong connections and facilitate easy, on demand release with a lower peel strength.

Additionally, the light switchable adhesive based connections points described herein hinder or prevent tampering with or circumvention of single-use components and systems, i.e., reusing one or more single use components of the therapy system.

Furthermore, in some implementations where strong adhesion to fragile surfaces is desired, a gentle release from the fragile surface can be achieved by employing light switchable adhesives. For example, a dressing including a light switchable adhesive can be exposed to light to switch the light switchable adhesive to a low-tack state and the light switchable adhesive can be removed from the fragile surface (tissue site of a patient) without harming the fragile surface. Thus, a light switchable adhesive attached to a patient can be "switched" and removed in a low or non-tacky state with less or no localized trauma or pain to the patient as compared to a conventional adhesive dressing and/or bandage that is removed from the patient in a high tack state. This is particularly true for patients with a long term condition that requires an adhesive dressing to be applied to the same part of the body repeatedly over a prolonged period, such as stoma patients. It is also true for patients with fragile skin, especially the elderly, children, immuno-compromised patients, etc.

In some implementations, one or more tubes of the therapy system are used to transport and deliver light to the light switchable adhesives. In some such implementations a light generating device, e.g., a UV torch/flashlight, is incorporated in a therapy device of the therapy system or is coupleable to a tube of the therapy system, such as a port thereof. Alternatively, one or more components of the therapy system have a window or light passing medium that enables light to be directed into one or more tubes of the therapy system. The light generating device, (e.g., a UVA light source) provides the light to one or more tubes which guide the light to the light switchable adhesive based connection points to trigger or activate the light switchable adhesive. Thus, components of the therapy system, such as a canister, tubes, and/or a dressing thereof, can be used as a light pipe or optical lumen to provide light through components of the therapy system to activate light switchable adhesive.

Additionally, or alternatively, connection points of therapy system includes covers, films, sheaths, and/or shrouds to prevent ambient light from triggering/activating the light switchable adhesives. Such light blocking elements can be used in addition to or in the alternative to a dedicated light device. For example, visible light switchable adhesives (i.e., light switchable adhesives that are switched by light in the visible light spectrum) can be used in connection points, and the connection points may include light blocking elements that are removed to activate the visible light switchable adhesive.

In some implementations, components of the therapy systems, such as a connector, include a mechanical alignment feature. For example, a first connector includes a pin (e.g., a guide pin) and a second connector includes an alignment slot or receptacle to receive the pin. In some such implementations, the mechanical alignment facilities alignment of the light switchable adhesive, bonding/mating surfaces of components, and/or internal lumens of components. In a particular implementation, components of the therapy systems, such as a connector, do not include a mechanical connection or interlocking feature. The lack of a mechanical connection or interlock feature, such as a pin and a "J" slot, prevents securing a connection point by mechanical means and possible reuse of the components by the mechanical means alone after the light switchable adhesive (e.g., a single-use adhesive) is activated.

In some implementations, a two-part light switchable adhesive is used to form a connection point. For example, the two-part light switchable adhesive is a chemically activated adhesive that forms a bond when two parts (e.g., components or compounds) interact with each other. To illustrate, a first connector has a coating or pattern of a first part (e.g., a sensitized adhesive or resin) of the two-part light switchable adhesive and a second connector has a coating or a pattern of second part (e.g., an activator or hardener) of the two-part light switchable adhesive. When the first component and the second component are pressed into contact, they activated to form a bond.

In some implementations, the light switchable adhesives described herein produce a visual indication when forming a bond or changing states. For example, the light switchable adhesives undergo a color change upon formation of a bond, upon transitioning from the first state to the second state, or both. To illustrate, the light switchable adhesive undergoes a color change when a bond is formed by two-part light switchable adhesives.

In some implementations, the light switchable adhesives described herein include photo initiators that are receptive to high wavelength UV light, such as UVC UV light. Such light switchable adhesives may not need covers or sheaths as ambient light does not typically include UVC light. For example, UVC light is not produced by commercial/conventional lighting devices used for illumination and UVC from the Sun is absorbed by the atmosphere.

Thus, the devices and systems of the present disclosure are configured to provide secure single-use connections and to hinder or prevent reuse of single-use components to reduce infection and contamination. Additionally, the devices and systems of the present disclosure are configured to provide easy assembly and disconnection with a low disconnection force enabling the young, elderly, and sick to easily connect and disconnect the devices and systems.

Some embodiments of the present apparatuses (e.g., a therapy system) comprise: a connection point including a connector having a light switchable adhesive provided on a mating portion of the connector; and a UV device configured to provide light to the light switchable adhesive via one or more components of the therapy system. In some implementations of the embodiments of the present apparatuses, the connection point comprises a connection point between a therapy device and a canister, between the canister and a set of tubes, within the set of tubes, between the set of tubes and a dressing, or between the dressing and a patient.

In some of the foregoing embodiments of the present apparatuses, the light switchable adhesive is configured to switch states based on first light, and further comprises a second light switchable adhesive, the second light switchable adhesive configured to switch states based on second light, where the second light corresponds to a different spectrum than the first light. In some implementations of the embodiments, the apparatuses further comprise a therapy device and a dressing in fluid communication with the therapy device.

In some of the foregoing embodiments of the present apparatuses, the apparatuses further comprise a light guide configured to transport light received by the dressing to adhesive coupled to the dressing. In some implementations of the embodiments, the present apparatuses further comprise a canister coupled to the therapy device and configured to receive fluid from the dressing.

In some implementations of the embodiments of the present apparatuses: the therapy device is configured to apply positive-pressure, reduced-pressure, or both to the dressing; and the UV device is incorporated in the therapy device, or the dressing. In some implementations of the embodiments of the present apparatuses, the therapy device comprises a controller configured to control operation of the therapy device, the UV device, or both.

Some embodiments of the present methods comprise: emitting UV light by a UV device; transmitting, by one or more components of a therapy system, the UV light to a light switchable adhesive of a connection point of the therapy system; and responsive to the UV light provided to the light switchable adhesive, transitioning from a first state to a second state by the light switchable adhesive. In some implementations of the embodiments, the methods further comprise disconnecting the connection point, where the second state has a lower peel strength than the first state.

In some of the foregoing embodiments of the present methods, the present methods further comprise, responsive to the UV light, changing color by the light switchable adhesive. In some implementations of the embodiments, the methods further comprise, prior to providing the UV light, connecting one of a therapy device, a canister, a tube, a connector, or a dressing to another one of the therapy device, the canister, the tube, the connector, or the dressing to form the connection point.

In some of the foregoing embodiments of the present methods, the present methods further comprise providing the UV light to a second light switchable adhesive of a second connection point of the therapy system. In some implementations of the embodiments, the methods further comprise receiving a code at a controller associated with the UV device, where the UV device emits the UV light responsive to receiving the code. In some implementations of the embodiments, the methods further comprise setting a timer associated with the UV device, where the UV device emits the UV light responsive to expiration of the timer.

In some of the foregoing embodiments of the present methods, the present methods further comprise: aligning a first component having a first part of a two-part light switchable adhesive and a second component having a second part of the two-part light switchable adhesive; and connecting the first component and the second component to form the connection point, where the first part and the second part are configured to form a bond responsive to being pressed together during connecting the first component and the second component, and where the two-part light switchable adhesive is configured to switch states to deactivate the bond when exposed to light.

In some of the foregoing embodiments of the present methods, the two-part light switchable adhesive switching states enables disconnection of the connection point, and aligning the first component and the second component includes aligning pin of the first component and a slot of the second component. In some implementations of the embodiments, the methods further comprise, prior to connecting, removing a cover film from the first component, the second component, or both.

Some embodiments of the present apparatuses (e.g., a tube connector) comprise: a connector body configured to define a mating portion, the mating portion configured to mate with a corresponding mating portion of a tube; and a light switchable adhesive coupled to the mating portion of the connector body. In some implementations of the embodiments of the present apparatuses, the mating portion of the connector body includes a female mating portion configured to receive the corresponding mating portion of the tube or a male mating portion configured to be inserted into the corresponding mating portion of the tube. The light switchable adhesive is configured to transition from a first state to a second state, and the light switchable adhesive has a first peel strength in the first state that is greater than a second peel strength of the light switchable in the second state.

In some of the foregoing embodiments of the present apparatuses, the apparatuses further comprise a second mating portion configured to receive a second tube or to be inserted into the second tube, where the tube connector comprises an in-line tube connector. In some implementations of the embodiments of the present apparatuses, the connector body is coupled to or incorporated with a canister, a therapy device, a tube, or a dressing. In some implementations of the embodiments, the apparatuses further comprise a cover film removably coupled to the light switchable adhesive.

In some of the foregoing embodiments of the present apparatuses, the apparatuses further comprise a shroud removably coupled to the connector body and configured to block ambient light from the light switchable adhesive. In some implementations of the embodiments of the present apparatuses, the light switchable adhesive is applied to the mating portion of the connector body as a coating. In other implementations of the embodiments of the present apparatuses, the light switchable adhesive is applied to the mating portion of the connector body in a pattern.

In some of the foregoing embodiments of the present apparatuses, the light switchable adhesive includes photo initiators configured to absorb or react with UV light, visible light, or both, and where the connector body is configured to transport received light through a channel defined by connector body. In some implementations of the embodiments of the present apparatuses, the connector body comprises a "Y" connector or a "T" connector.

Some embodiments of the present apparatuses (e.g., a tube) comprise: a body configured to define at least one lumen; and a light switchable adhesive coupled to a mating portion of the body. In some implementations of the embodiments, the apparatuses further comprise a sheath coupled to an exterior surface of the body of the tube, the sheath configured to reflect light within the tube, block light from entering the tube, or both.

In some of the foregoing embodiments of the present apparatuses, the light switchable adhesive is provided on an exterior surface of the body of the tube. Additionally, or alternatively, the light switchable adhesive is provided on an interior surface of the body of the tube.

In some of the foregoing embodiments of the present apparatuses, the apparatuses further comprise a cover film removeably coupled to the light switchable adhesive. In some implementations of the embodiments of the present apparatuses, the body is optically transparent, the body comprises a colored polymer material, the body is flexible and includes polymer material, or a combination thereof.

In some of the foregoing embodiments of the present apparatuses, the body defines multiple lumens, the multiple lumens including the at least one lumen. In a particular implementation, the multiple lumens are arranged coaxially, side-by-side, or bundled. Additionally, or alternatively, the multiple lumens include an optical lumen configured to transport light to activate the light switchable adhesive. In a particular implementation, the optical lumen includes a colored polymer material or a sheath. In some of the foregoing embodiments of the present apparatuses, an exterior wall of the body of the tube, the at least one lumen, or both, are configured to reflect light to transport the light within the tube.

Some embodiments of the present apparatuses (e.g., a dressing) comprise: a connector body configured to receive light; a light switchable adhesive coupled to the dressing; and a drape coupled to the connector body and including an optical channel configured to receive the light from the connector body and provide the light to the light switchable adhesive. In some implementations of the embodiments, the apparatuses further comprise a shroud coupled to an exterior surface of the drape of the dressing, the shroud configured to reflect light within the dressing, block light from entering the dressing, or both.

In some implementations of the embodiments of the present apparatuses: the light switchable adhesive is configured to couple the drape to a tissue site; and the optical channel is configured to provide the light to the light switchable adhesive to decouple the light switchable adhesive from the drape, to decouple the light switchable adhesive from the tissue site, or both.

Some embodiments of the present apparatuses (e.g., a therapy system) comprise: a canister comprising: a connection port configured to couple to a connector or a tube; and a canister body including light transmission means for passing light and providing the light to the connection port. In some implementations of the embodiments, the apparatuses further comprise a UV device coupled to the canister body and configured to emit the light to the light transmission means. Additionally, or alternatively, the apparatuses further comprise a therapy device configured to couple to the canister, the therapy device includes a UV device configured to emit the light to the light transmission means.

As used herein, the term "switchable" will be used to refer to adhesives which can be changed from a high tack and/or peel strength state to a low tack and/or peel strength state (e.g., non-tacky state). Recognizing that the expression "low tack and/or peel strength" is a relative term, it will be defined here as meaning a condition of a minimum reduction in tackiness which the adhesive reaches after switching from the high tack and/or peel strength state. The reduction in tack or peel force may be as great as 99% or as little as 30%. Typically, the reduction in tack or peel force is between 70%. and 90%.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of—rather than comprise/have/include-any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 2A is a side view of an example of a connection point of a system for wound therapy;

FIG. 2B is a cross-sectional view of an example of a connector of the connection point of FIG. 2A taken along line A-A of FIG. 2A;

FIG. 2C is a side view of an example of a connection point of a system for wound therapy;

FIG. 2D is a side view of an example of a connection point of a system for wound therapy;

FIG. 3A is side view of an example of a connection point of a system for wound therapy;

FIG. 3B is a cross-sectional view of an example of a connector of the connection point of FIG. 3A taken along line B-B of FIG. 3A;

FIG. 3C is side view of an example of a connection point of a system for wound therapy;

FIG. 3D is side view of an example of a connection point of a system for wound therapy;

FIG. 7A is diagram of an example a system for wound therapy;

FIG. 7B is a cross-sectional view of an example of a tube taken along line D-D of FIG. 7A;

DETAILED DESCRIPTION

Figure 1:
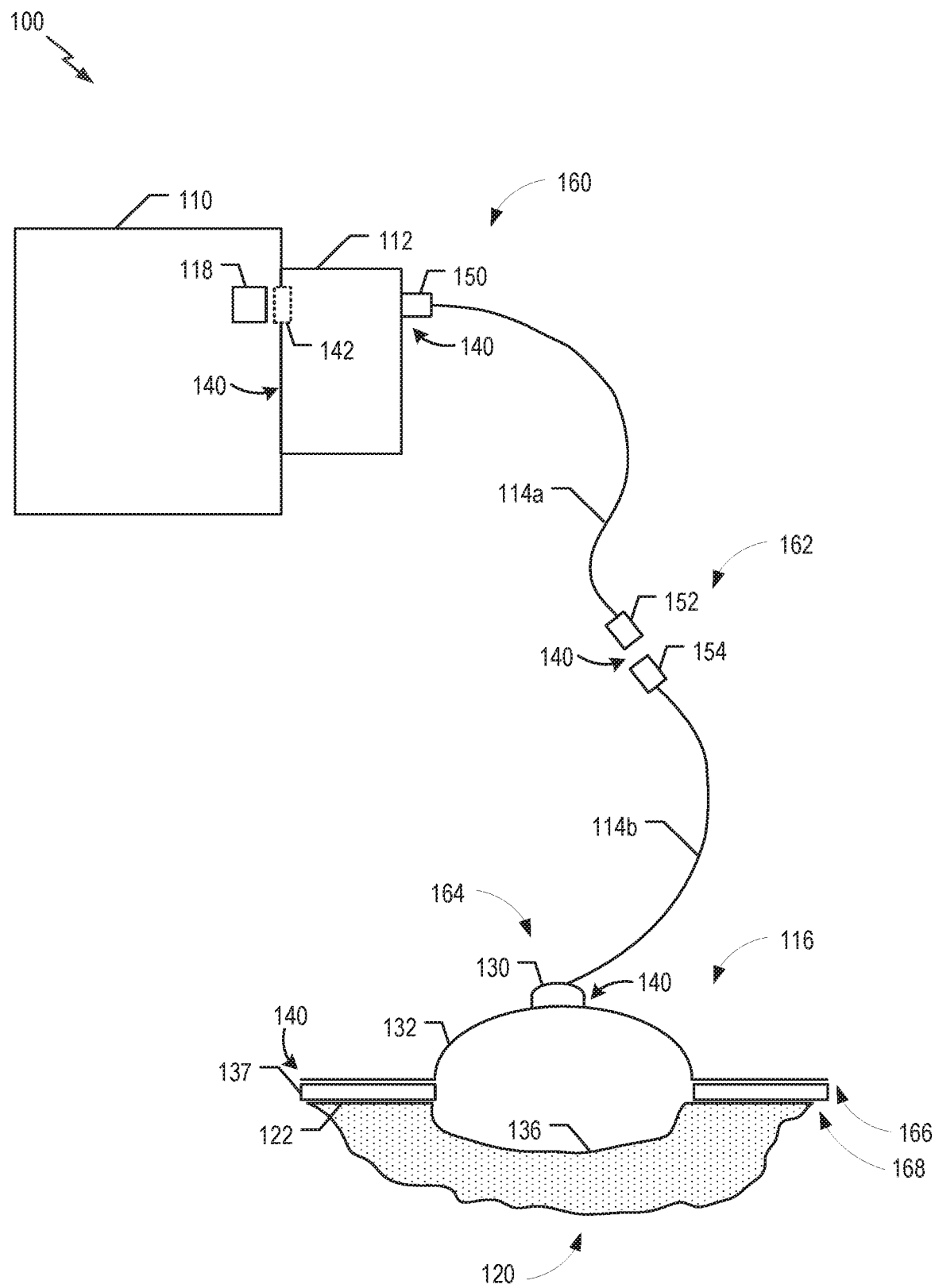
FIG. 1 is a schematic view of an example of a system for wound therapy.

As used herein, the terms "tissue site" and "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The terms "tissue site" and "target tissue" as used herein can also refer to a surrounding tissue area(s) and/or areas of tissue that are not necessarily wounded or exhibit a disorder, but include tissue that would benefit from tissue generation and/or tissue that may be harvested and transplanted to another tissue location. The terms "tissue site" and "target tissue" may also include incisions, such as a surgical incision. In some implementations, "target tissue" may correspond or refer to a wound, and "tissue site" may correspond or refer to a tissue area(s) surrounding and including the target tissue. Additionally, the term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft. A wound may include chronic, acute, traumatic, subacute, and dehisced wounds, partial-thickness burns, ulcers (such as diabetic, pressure, or venous insufficiency ulcers), flaps, grafts, and fistulas, for example.

The term "positive-pressure" (or "hyperbaric") as used herein generally refers to a pressure greater than a local ambient pressure, such as the ambient pressure in a local environment external to a sealed therapeutic environment (e.g., an internal volume). In most cases, this positive-pressure will be greater than the atmospheric pressure at which the patient is located. Alternatively, the positive-pressure may be greater than a hydrostatic pressure associated with tissue at the tissue site. Unless otherwise indicated, values of pressure stated herein are gauge pressures. References to increases in positive-pressure typically refer to an increase in absolute pressure, and decreases in positive-pressure typically refer to a decrease in absolute pressure. Additionally, the process of increasing pressure may be described illustratively herein as "applying", "delivering," "distributing," "generating", or "providing" positive-pressure, for example.

The term "reduced-pressure" (and "negative-pressure" or "hypobaric") as used herein generally refers to a pressure less than a local ambient pressure, such as the ambient pressure in a local environment external to a sealed therapeutic environment (e.g., an internal volume). In most cases, this reduced-pressure will be less than the atmospheric pressure at which the patient is located. Alternatively, the reduced-pressure may be less than a hydrostatic pressure associated with tissue at the tissue site. Unless otherwise indicated, values of pressure stated herein are gauge pressures. References to increases in reduced-pressure typically refer to a decrease in absolute pressure, and decreases in reduced-pressure typically refer to an increase in absolute pressure. Additionally, the process of reducing pressure may be described illustratively herein as "applying", "delivering," "distributing," "generating", or "providing" reduced-pressure, for example.

The term "fluid" may refer to liquid, gas, air, or a combination thereof. The term "fluid seal," or "seal," means a seal adequate to maintain a pressure differential (e.g., positive-pressure or reduced-pressure) at a desired site given the particular pressure source or subsystem involved. Similarly, it may be convenient to describe certain features in terms of fluid "inlet" or "outlet" in such a frame of reference. However, the fluid path may also be reversed in some applications, such as by substituting a reduced-pressure source (negative or hypobaric pressure source) for a positive-pressure source, and this descriptive convention should not be construed as a limiting convention.

FIG. 1. shows a schematic view of an illustrative system 100 (e.g., a therapy system) for wound therapy. System 100 may include a therapy device 110, a canister 112, one or more tubes 114, a dressing 116, and a UV device 118. System 100 is configured to provide a treatment to a tissue site 120 associated with a target area of a patient. For example, system 100 may be configured to remove fluid from (and/or provide fluid to) tissue site 120. To illustrate, dressing 116 may be in fluid communication with tissue site 120 and may be in fluid communication with therapy device 110 via the one or more tubes 114. In some implementations, system 100 may include one or more components commercially available through and/or from KCI USA, Inc. of San Antonio, Tex., U.S.A., and/or its subsidiary and related companies (collectively, "KCI").

System 100 includes one or more interfaces between components (e.g., 110-118) of system 100, between sub-components of a component, or between a component of system 100 and a patient, referred to herein as connection points. As illustrated in FIG. 1, five exemplary connection points are illustrated as connection points 160-168. Additionally, in the example of FIG. 1 each of connection points 160-168 is formed using light switchable adhesive (LSA 140). Forming connection points with LSA 140 enables secure, strong, single-use bonds to be formed, which can be activated using light to weaken the LSA 140 and enable disconnection of the connection point. Connection points 160-168 and LSA 140 are described further herein.

Therapy device 110 is configured to provide a treatment to tissue site 120. As illustrated in the example of FIG. 1, therapy device 110 includes or corresponds to a negative-pressure treatment apparatus and is configured generate and provide negative pressure to tissue site 120. Providing negative pressure to tissue site 120 enables sealing of target tissue 136 with dressing 116, increases adhesion of dressing 116 (e.g., adhesive thereof, such as adhesive 137) to tissue site 120, enables fluid removal from tissue site 120 (e.g., exudate from target tissue 136), or a combination thereof.

In other implementations, therapy device 110 is configured to provide a fluid to tissue site 120. For example, therapy device 110 includes or correspond to a positive-pressure treatment apparatus and is configured to provide oxygen at a positive-pressure via tube 114 and dressing 116. For example, therapy device 110 may include a positive-pressure source, such as a pressurized oxygen container, an oxygen concentrator, or an oxygen collector (e.g., a pump and a filter) and/or the like, configured to be actuatable (and/or actuated) to apply positive-pressure (e.g., hyperbaric pressure) to dressing 116. As another example, therapy device 110 includes or corresponds to a medication delivery device and is configured to deliver medication to tissue site 120.

Canister 112 is configured to be removeably coupleable with therapy device 110. For example, canister 112 is configured to couple to therapy device 110 by a mechanical connector. Canister 112 is configured such that while canister 112 is coupled to therapy device 110, canister 112 is in fluid communication with therapy device 110 (e.g., a pump and one or more lumens or tubes thereof). Thus, therapy device 110 can use canister 112 to collect fluids from or deliver fluids to dressing 116 via one or more tubes 114. For example, exudate, fluid, and/or another material removed from tissue site 120 may be collected in canister 112 for disposal. In other implementations, canister 112 is integrated with or fixedly coupled to therapy device 110.

One or more tubes 114 are configured to couple therapy device 110 to dressing 116. As illustrated in FIG. 1, system 100 includes two tubes 114, i.e., a first tube 114a and a second tube 114b. In FIG. 1, first tube 114a is configured to couple to canister 112 and to second tube 114b, and second tube 114b is configured to couple to first tube 114a and to dressing 116. In other examples, system 100 includes one tube 114 or more than two tubes 114. As illustrated in the example of FIG. 1, first tube 114a is coupled to a connector 150 of canister 112 and second tube 114b is coupled to a connector 130 of dressing 116. The connectors 130, 150 may be formed integrally with the canister 112 or dressing 116, or may be coupleable with the canister 112 or dressing 116. In other implementations, tube 114a, tubes 114b, or both, may be coupled to ports recessed in canister 112 or dressing 116 or fixed to (e.g., formed integrally with) canister 112 or dressing 116.

As used herein, a "tube" broadly refers to a tube, pipe, hose, conduit, or other structure with one or more lumens adapted to convey fluid, exudate, and/or the like, between two ends. In some implementations, a tube may be an elongated, cylindrical structure with some flexibility; however, a tube is not limited to such a structure. Accordingly, tube may be understood to include multiple geometries and rigidities.

One or more tubes 114 include one or more lumens (e.g., one or more through conduits), such as a single lumen conduit or multiple single-lumen conduits. One or more tubes 114 (e.g., a least one of the one or more lumens thereof) are configured to enable fluid communication between therapy device 110 and dressing 116. For example, fluid(s) and/or exudate can be communicated between therapy device 110 and dressing 116, and/or one or more pressure differentials (e.g., negative-pressure, positive-pressure, or both) can be applied by therapy device 110 to dressing 116. As an illustrative, non-limiting illustration, one or more tubes 114 are configured to transport (e.g., remove) fluid from dressing 116 to canister 112 to establish negative-pressure. Communication of fluid(s) and application of a pressure differential can occur separately and/or concurrently.

In some implementations, one or more tubes 114 may include multiple lumens, such as a primary lumen (e.g., a pressure/fluid lumen) for application of a first pressure differential (e.g., negative-pressure) and/or communication of fluid, and one or more secondary lumens proximate to or around the primary lumen. The one or more secondary lumens (e.g., one or more ancillary/peripheral lumens) may be coupled to one or more sensors (of therapy device 110), coupled to one or more valves, as an illustrative, non-limiting example. Examples of multi-lumen tubes are described further with reference to FIGS. 6A, 6B, 7A, and 7B. Although the one or more tubes 114 are described as a set of tubes to couple therapy device 110 to dressing 116, in other implementations, system 100 may include multiple sets of tubes 114, such as multiple distinct tubes 114 coupled to one or more of therapy device 110, dressing 116, canister 112, another therapy component, or a combination thereof, to one or more other components of system 100.

In some implementations, at least one tube of the one or more tubes 114 includes or corresponds to a transparent (e.g., clear) plastic tube. In other implementations, at least one tube of the one or more tubes 114 includes or corresponds to a colored tube, such as a colored polymer tube. Colored tubes may have higher a reflectance or refractance (e.g., a higher index of reflectance or refractance) to a particular type of light, such as UV light. The colored polymer material may block (e.g., reflect or absorb) transmission of ambient light from outside of the one or more tubes 114 from entering the one or more tubes 114. Blocking light from entering the one or more tubes 114 reduces or prevents the light from being transmitted to the LSA 140 of system 100.

The one or more tubes 114 may be formed by extrusion. In a particular implementation, at least one tube of the one or more tubes 114 includes an outer sheath (e.g., sheath 514 of FIG. 5), such as a sheath similar to a sheath of a fiber optic cable. The outer sheath may include or correspond to a tubular cover, a coating, or a colored polymer layer. The outer sheath has a greater reflectance and/or refraction than the one or more tubes 114, and thus increases light reflection/refraction within the one or more tubes 114 and reduces light transmission through walls (e.g., out) of the one or more tubes 114.

In some implementations, the one or more tubes 114 themselves, i.e., outer walls thereof and/or one or more lumens thereof, are configured to transport the light. In such implementations, one or more of the lumens may have other functions and correspond to pressure therapy lumens, fluid delivery lumens, fluid removal lumens, etc. In other implementations, the one or more tubes 114 include a dedicated lumen (e.g., an optical lumen, a waveguide lumen, etc.)

configured to transport light. In some such implementations, the dedicated lumen includes an outer sheath or is made from another material with a higher reflectivity, higher refractivity, lower transmission, lower absorption, or a combination thereof, to the light being transported than a second material of the one or more tubes 114 (e.g., another lumen thereof).

In some implementations, at least one tube 114 of the one or more tubes 114 includes or is made from a high refractive material, such as a material with a refractive index that is greater than 1.6. In a particular implementation, high refractive material has a refractive index greater than or equal to 1.7. In other implementations, a sheath (e.g., sheath 514 of FIG. 5) of high refractive material is coupled to the at least one tube 114, as described further with reference to FIG. 5.

Dressing 116 is coupleable with at least one tube of the one or more tubes 114 and includes a connector 130 (also referred to as a dressing connection pad or a pad) and a drape 132. Dressing 116 may further include a manifold (also referred to as a distribution manifold or an insert), as described further with reference to FIGS. 6A and 7A. Connector 130 is configured to be coupled to at least one tube of the one or more tubes 114. Drape 132 may be coupled to connector 130. To illustrate, drape 132 may be coupled to connector 130 via an adhesive, a separate adhesive drape over at least a portion of connector 130 and at least a portion of drape 132, or a combination thereof, as illustrative, non-limiting examples.

Drape 132 may be configured to couple dressing 116 at tissue site 120 and/or to provide a seal to create an enclosed space (e.g., an interior volume) corresponding to tissue site 120. For example, drape 132 may be configured to provide a fluid seal between two components and/or two environments, such as between a sealed therapeutic environment and a local ambient environment. To illustrate, when coupled to tissue site 120, drape 132 is configured to maintain a pressure differential (provided by therapy device 110 or another pressure source) at tissue site 120. Additionally, drape 132 may seal or block ambient light from transmission to tissue site 120 and/or adhesives attached thereto. Drape 132 includes a drape aperture that extends through drape 132 to enable fluid communication between therapy device 110 and target tissue 136, as described further with reference to FIG. 7A.

As shown, drape 132 is coupled to tissue site 120 via a representative adhesive 137, such as a medically acceptable, pressure-sensitive adhesive that extends about a periphery, a portion, or an entirety of drape 132. Additionally, or alternatively, drape 732 may be coupled to tissue site 720 via a double-sided drape tape, paste, hydrocolloid, hydrogel, and/or other sealing device or element, as illustrative, non-limiting examples. In some implementations, drape 132 includes a cavity or conduit to transport and/or diffuse received light to adhesives (e.g., adhesive 137) attached to drape 132 and/or tissue site 120, as described further with reference to FIGS. 5 and 6A.

System 100 further includes LSA 140 at one or more connection points 160-168 between components of system 100. LSA 140 includes one or more photo initiators and is configured to switch states upon exposure to light of a particular spectrum or wavelength. The photo initiators are configured to absorb light (of particular spectrum or wavelength) and cross link with each other and/or free radicals to reduce tackiness, increase brittleness, increase fragility, reduce ductileness, change color, or a combination thereof. Thus, LSA 140 transitions from a first state (e.g., high tack state) to a second state (e.g., a low tack, no tack, or cross linked state) upon exposure to light. Transitioning from the first state to the second state enables easy, pain and trauma free removal of the dressing and/or easy disconnection of a connection point. Further, because the LSA 140 cannot switch back to the first state from the second state, the LSA 140 decreases and/or prevents reusing of single-use components of system 100.

In some implementations, LSA 140 includes UV photo initiators and is configured to absorb UV light (light from at least a portion of the UV spectrum) and switch states. In other implementations, LSA 140 includes visible light photo initiators and is configured to absorb visible light (light from at least a portion of the visible light spectrum) and switch states. As illustrated in FIG. 1, LSA 140 can be used to at one or more connection points 160-168. LSA 140 may be formed with one or components of system 100, such as co-extruded with a material of the one or more components. Alternatively, LSA 140 may be applied to the one or more components of system 100, e.g., extruded after formation of the one or more components. In some implementations, LSA 140 is a coating or a pattern of coatings, as described further with reference to FIG. 4C. In some such implementations where mechanical guides (e.g., a pin and a slot) are used, the mechanical guides may align the LSAs 140 (or patterns thereof).

In some implementations, LSA 140 includes a UV marking additive. In a particular implementation, the UV marking additive includes or corresponds to an ultraviolet absorber (UV absorber). A UV absorber is a molecule used in organic or synthetic materials to absorb UV radiation. The UV absorbers are configured to absorb at least a portion of UV radiation of the UV spectrum and produce a visual indication, such as a color change. For example, UVA absorbers are configured to absorb UVA radiation, i.e., electromagnetic radiation having wavelengths between 300 and 400 nm.

UV device 118 is configured to generate UV light to activate LSA 140 (photo initiators thereof) and cause LSA 140 to switch states. For example, UV device 118 includes or corresponds to a UV light source configured to generate light or electromagnetic radiation having a wavelength of 10-400 nanometers. In some implementations, UV device 118 may include or correspond to a UV torch. For example, UV torch may include one or more LEDs configured to generate incoherent light in the UV spectrum. In a particular implementation, UV torch generates light in a particular subspectrum of the UV spectrum, such as UVA or UVC.

In other implementations, UV device 118 may include or correspond to a UV Laser, such as a gas laser, a laser diode, a solid-state laser, an excimer laser, or a combination thereof. In some implementations, UV laser is configured to generate coherent light (e.g., a laser beam) having electromagnetic radiation of UV wavelengths. For example, UV laser is a UVA laser (315-400 nm), a UVB laser (280-315 nm), a UVC laser (100-280 nm), or an extreme UV laser (10-121 nm).

UV device 118 may be integrated with a component of system 100, such as therapy device 110, as illustrated in FIG. 1. In the example illustrated in FIG. 1, UV device 118 generates UV light and directs the UV light to UV light passage 142. UV light passage 142 (e.g., a window or light passing medium) is configured to enable the UV light to pass. UV light passage 142 may optionally include one or more components to direct or focus the UV light, such as one or more lens, refractors, collimators, etc.

Figure 5:
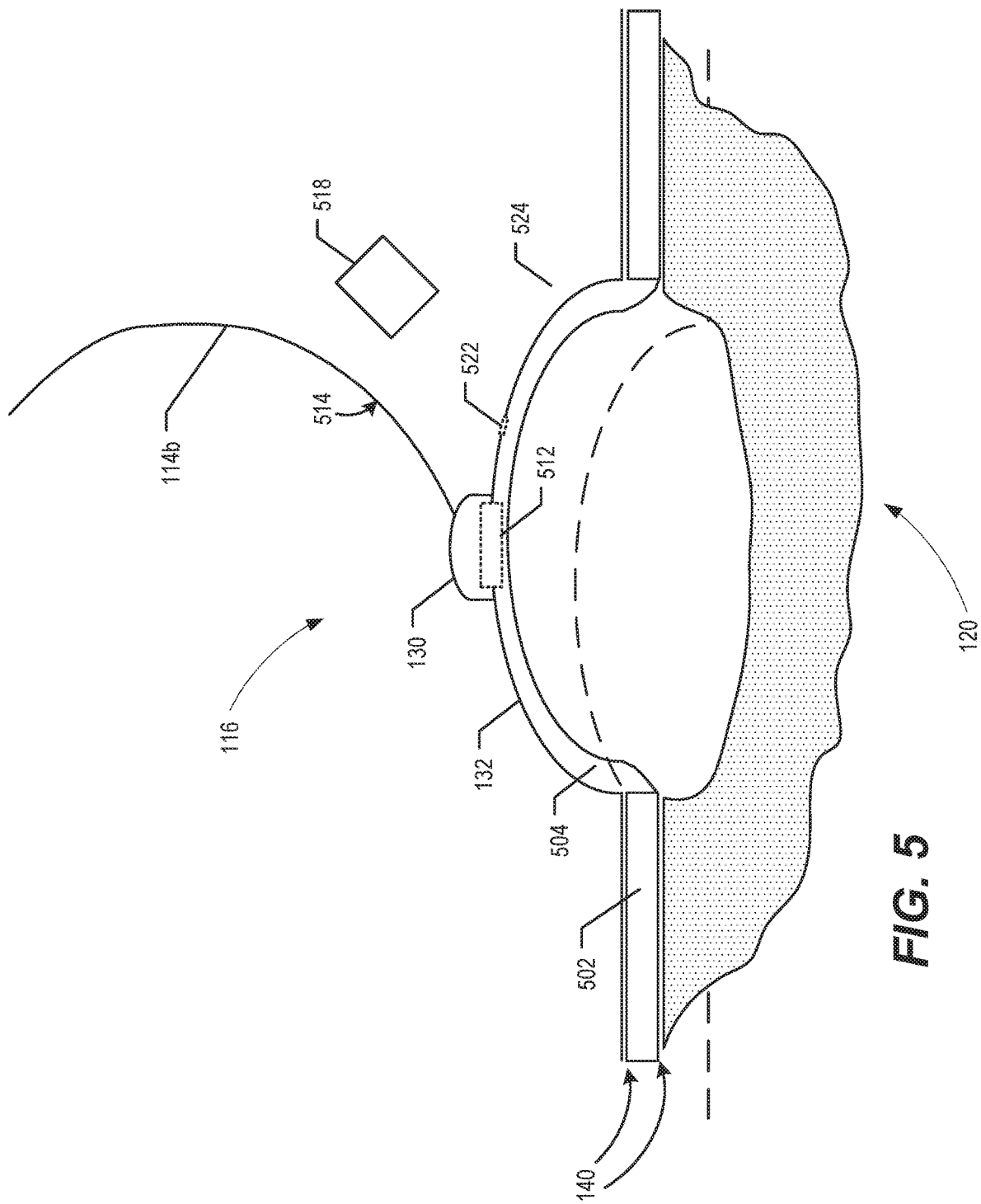
FIG. 5 is a schematic view of an example of a dressing for wound therapy.

In other implementations, UV device 118 is integrated with another component of system 100, such as a dressing 116 as illustrated in FIG. 5. Alternatively, UV device 118 may be a separate or dedicated device that is coupleable with a component of system 100. For example, UV device 118 may be coupleable with a tube of the one more tubes 114, dressing 116, or a connector, such as one of connectors 130, 150, 152, or 154. To illustrate, a component of system 100 includes a port or a window (e.g., 522 of FIG. 5) configured to receive UV device 118. The port or window may include a cover or film to reduce or prevent light from entering the port or window when the UV device 118 is not coupled to the port or the window is not in use.

System 100 may optionally include one or more connectors to couple components of system 100 to each other. As illustrated in FIG. 1, system 100 includes connectors 150, 152, and 154. In FIG. 1, connector 150 corresponds to a component connector and connectors 152 and 154 corresponds to tube connectors (e.g., in-line tube connectors). Connector 130 of dressing 116 may include or correspond to a connector of system 100, or may include an additional connector (e.g., one of connectors 150, 152, and 154) to couple with a tube of the one or more tubes 114. In other implementations, system 100 does not include one or more of connectors 130, 150, 152, 154. For example the one or more tubes 114 can be inserted into ports of (or integrated into) other components of system 100.

Connectors 130, 150, 152, 154 are configured to join components of system 100 together to form connection points 160-166. One or more of the connection points 160-168 may include LSA 140. As illustrated in FIG. 1, each connection point 160-168 includes LSA 140.

First connection point 160 is a connection (e.g., interface) between canister 112 and tube 114a. Second connection point 162 is a connection between tube 114a and 114b. As illustrated in FIG. 1, second connection point 162 is a connection between connector 152 of tube 114a and connector 154 of tube 114b. Third connection point 164 is a connection between tube 114b and dressing 116. As illustrated in FIG. 1, third connection point 164 is a connection between connector 154 of tube 114b and connector 130 of dressing 116.

Fourth connection point 166 is a connection between components of dressing 116. As illustrated in FIG. 1, fourth connection point 166 is a connection between drape 132 of dressing 116 and adhesive 137, which is attachable to tissue site 120. Fifth connection point 168 is a connection between dressing 116 and tissue site 120. As illustrated in FIG. 1, fifth connection point 168 is a connection between adhesive 137 and tissue surface 122. If fourth connection point 166 is present, adhesive 137 may be integrated with or attached to dressing 116 or may be detached from dressing 116. Various examples of connectors 130, 150, 152, 154 and connection points 160-168 are described further with reference to FIGS. 2A-2D, 3A-3D, and 4A-4C.

Prior to operation of therapy device 110, system 100 may be setup, i.e., coupled together. To illustrate, one or more components of system 100 may be provided individually and can be combined with each other to form system 100 or system 100 can be provided as a disassembled kit which is assembled by a patient or a care provider (referred to herein as a user). Although described in order from therapy device 110 to dressing 116, system 100 can be setup in any order, and one or more of the connection points 160-168 of FIG. 1 may not be present. For example, FIG. 1 illustrates a modular system with five connection points 160-168. In other implementations, only a single connection point is used or other (i.e., additional) connection points may be used, such as a connection point between therapy device 110 and canister 112.

Accordingly, an exemplary setup of system 100 includes coupling tube 114a to canister 112 (which is provided with or attached to therapy device 110) to form first connection point 160. Specifically, connector 150 of tube 114a is coupled to a port or connector of canister 112. Alternatively, tube 114a is directly coupled to (inserted into) a port or connector of canister 112. Thus, tube 114a is coupled to therapy device 110 via canister 112 and is in fluid communication with therapy device 110 and canister 112. In other implementations, canister 112 is separate from therapy device and prior to forming the first connection point, canister 112 is coupled to therapy device 110.

Tube 114a is coupled to tube 114b to form the second connection point 162. Specifically, connector 152 of tube 114a is coupled to connector 154 of tube 114b. Alternatively, tube 114a is directly coupled to (inserted into) connector 154 or tube 114b is directly coupled to connector 152. Tube 114b is coupled to dressing 116 to form the third connection point 164. As illustrated in FIG. 1, tube 114b is inserted into a cavity or opening defined by connector 130 of dressing 116. Thus, dressing 116 is coupled to therapy device 110 via canister 112 and one or more tubes 114, and dressing 116 is in fluid communication with therapy device 110, canister 112, and one or more tubes 114.

Dressing 116 is coupled to adhesive 137 to form the fourth connection point 166. In other implementations, adhesive 137 is provide with dressing 116 (e.g., drape 132 thereof). Dressing 116 and adhesive 137 are coupled to tissue site 120 to form the fifth connection point 168. Thus, therapy device 110 and tissue site 120 are in fluid communication and therapy device 110 can provide treatment to tissue site 120. As explained above, the forgoing description is one exemplary setup of system 100. In other implementations, connection points 160-168 may be formed in any order. For example, the connection points 160-168 may be formed in reverse order, starting from the fifth connection point 168 and finishing with the first connection point 160.

System 100 can then be operated by the patient and/or the care provider. Operation of therapy systems, such as system 100, is described with reference to FIGS. 6A and 7A. After operation of system 100, such as therapy device 110 or upon reaching an end of life for a component of system 100, such as canister 112, one or more components of system 100 can be disconnected. For illustrative purposes, a full disconnect of system 100 will be described. In other implementations, less than all connection points are disconnected (e.g., a single connection point is disconnected) and a new or replacement component is coupled to system to form a new connection point, and thus operation of system 100 can resume.

As an illustrative example of a full disconnect, after operation of therapy device 110, system 100 is disconnected from tissue site 120 to therapy device 110. The order of disconnection, like the order of connection, is interchangeable and will be described starting from the tissue site 120 and working towards therapy device 110. After operation of therapy device 110 or upon reaching end of life of a particular component, UV device 118 is activated. In some implementations, UV device 118 is activated by a button on therapy device 110 or UV device 118. In other implementations, UV device 118 is activated remotely, e.g., wirelessly by a remote control device or a mobile device (e.g., a smartphone). In a particular implementation, UV device 118 is activated upon entry of a code. In some such implementations, the code or the remote control device for UV device 118 activation is controlled by medical professionals or authorized users. In other implementations, UV device 118 is activated up expiration of a timer or upon reaching a particular set time, i.e., activated after a set time period or duration. Thus, by employing remote control, codes, passwords, timers, etc., UV device 118 can be configured to be activated or controlled by an authorized person (e.g., a care provider), and UV device 118 or system 100 can reduce or prevent accidental or unauthorized activation or control.

Upon activation of UV device 118, UV device 118 emits UV light and the UV light travels through UV passage 142 and canister 112 into tube 114*a*, where the UV light activates LSA 140 of first connection point 160. The UV light travels through tube 114*a* by reflecting off walls of tube 114*a* and/or walls of the one or more lumens thereof. The UV light travels from tube 114*a* to tube 114*b*, where the UV light activates LSA 140 of second connection point 162, and through tube 114*b*. The UV light travels from tube 114*b* to connector 130 of dressing 116, where the UV light activates LSA 140 of third connection point 164. The UV light travels from connector 130 through dressing 116 to adhesive 137, where the UV light activates the adhesive 137 (e.g., the LSA 140 thereof) and connection points 166, 168. Transportation of light through dressing 116 is further described with reference to FIGS. 5 and 6A.

After a time period or responsive to user control, UV device 118 ceases emitting UV light. The UV light emitted by the UV device 118 "activates" LSA 140 and causes LSA 140 of connection points 160-168 to switch from the first state to the second state. After the LSA 140 has transitioned to the second state (e.g., low tack or low peel strength state), the user can easily disconnect connection points 160-168. A time period or duration of UV device 118 on-time, LSA 140 exposure or transition time, or a combination thereof, may be indicated by the therapy device 110, by the LSA 140, or both. To illustrate, the therapy device 110 can include a timer configured to indicate a UV device 118 activation time, a waiting time (a time period or duration between deactivation of UV device 118 and recommended disconnect of components). As another illustration, LSA 140 is configured to change colors or produce another visual indication upon switching from the first state to the second state. The LSA 140 color change or visual indication can provide an indication of deactivation of UV device 118, disconnection of components, or both.

After a time period or an indication, a user disconnects connection points 160-168. As an illustrative example, user disconnects adhesive 137 from tissue site 120 and/or drape 132 from adhesive 137 to disconnect connection points 166, 168. User disconnects tube 114*b* from connector 130 to disconnect third connection point 164 and disconnects tube 114*b* from tube 114*a* to disconnect second connection point 162. User disconnects tube 114*a* from canister 112 to disconnect first connection point 160, and optionally, user disconnects canister 112 from therapy device 110.

As explained above, in other implementations, user performs only a partial disconnection of one or more components of system 100. For example, one or more components of system 100 may be disconnected and the other components reused. For example, multiple dressings 116 may be used (connected to and disconnected from system 100) before canister 112 is filled and is disconnected from system 100. As another example, multiple canisters 112 may be used (connected to and disconnected from system 100) before a single dressing 116 is changed (connected to and disconnected from system 100).

To facilitate replacement of a single component or a subset of components (i.e., activation of a single connection point or a subset of connection points), a separate UV device can be utilized, a low power setting of UV device 118 can be used, light blocking elements (e.g., cover films, shrouds, etc.) can be utilized, or a combination thereof. For example, in addition to or in the alternative to the UV device 118 in therapy device 110, a second UV device (e.g., 518 of FIG. 5) can be used to direct light to a particular connection point including LSA 140 or a subset of connection points including LSA 140. To illustrate, the second or separate UV device can be used to direct UV light to a window or port (e.g., 522 of FIG. 5) associated with second connection point 164 to disconnect tube 114*b* from dressing 116 and facilitate replacement of dressing 116.

As another illustration, the second or separate UV device (e.g., second light device 518 of FIG. 5) can be used to direct UV light to a window or port (e.g., 522 of FIG. 5) associated with first connection point 160 to disconnect tube 114*a* from canister 112 and facilitate replacement of canister 112 or a low power setting of UV device 118 can be used such that emitted UV light only travels to first connection point 160 in sufficient intensity to cause a state switch of LSA 140 of first connection point 160 (and not to cause a state switch of LSA 140 of connection points 162-168). As another example, a tube of the one or more tubes 114 may include a port or a window (e.g., 522 of FIG. 5) configured to receive UV device 118 or the second light device or may include a passage 142 to direct light into (either from UV device 118, the second light device, or an ambient source) the tube.

Additionally, or alternatively, one or more components of system 100 may include one or more light blocking elements (e.g., a cover film, shroud, or barrier layer, such as shroud 524 of FIG. 5) which blocks light (ambient, device light, or both) from activating one or more LSAs 140 of system 100. Light blocking elements may facilitate replacement of a single component or a subset of components (i.e., activation of a single connection point or a subset of connection points) or use of a visible light device or ambient light to activate LSA 140.

In some implementations, system 100 includes both a UV device 118 and a visible light device, such as second light device 518 of FIG. 5. Employing two light sources enables use of two or more different LSAs and activation of select LSAs (e.g., UV and visible light LSAs) and disconnection of select connection points without cover films and/or extra ports. In ambient light embodiments, light blocking elements and/or focusing or gathering element can be used. For example, a lens can be used to focus ambient light to expose LSA 140 to a sufficient amount or intensity of light to initiate a transition, cover films or shrouds can be removed to expose LSA 140 to light, or both.

Additionally, or alternatively, canister 112 is configured to couple to therapy device 110 by an adhesive, such as light switchable adhesive 140. In such implementations, canister 112 is designed to be a single-use component. To illustrate, when canister 112 is filled with fluid removed from tissue site 120, canister 112 is disconnected from therapy device 110 and disposed of. A new canister 112 (e.g., a sterile canister) can be coupled to therapy device 110 to resume treatment. In a particular implementation, the light switchable adhesive 140 is applied to the canister 112, such that the therapy device 110 is reusable and can accommodate multiple single-use canisters 112. To illustrate, when the light switchable adhesive 140 is activated, the light switchable adhesive 140 remains on the canister 112 after deactivation and the therapy device 110 can be coupled to another canister 112. In other implementations, canister 112 is separate from therapy device 110 or incorporated within therapy device 110. In other implementations, canister 112 includes UV device 118.

In a particular implementation, system 100 includes a connection point (e.g., 160-168) including a connector (e.g., 130, 150, 152, 154) having LAS 140 provided on a mating portion of the connector and a UV device 118 configured to provide light to the LSA 140 via one or more components (e.g., 110-118) of system 100.

Thus, system 100 (e.g., one or more of the components thereof) is configured to provide secure single-use connections and to hinder or prevent reuse of single-use components to reduce infection and contamination. Additionally, system 100 (e.g., one or more of the components thereof) configured to provide easy assembly and disconnection with a low disconnection force enabling the young, elderly, and sick to easily connect and disconnect the devices and systems.

Figure 4A:
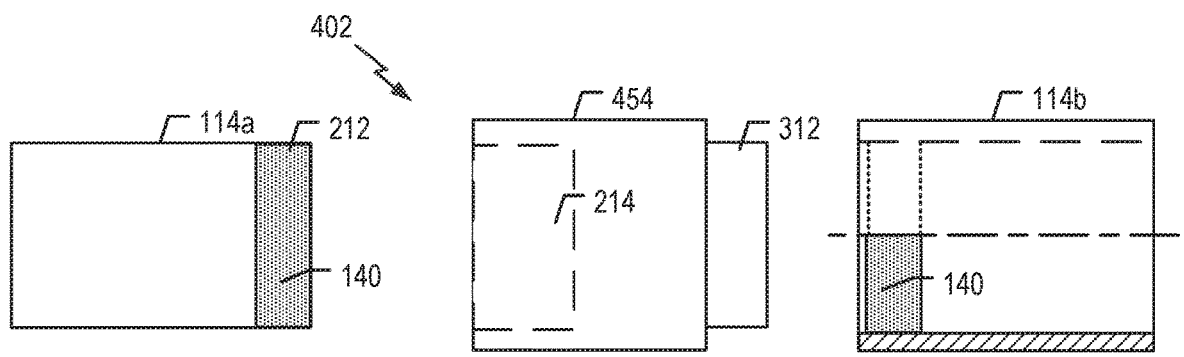
FIG. 4A is side view of an example of a connection point of a system for wound therapy.
Figure 4B:
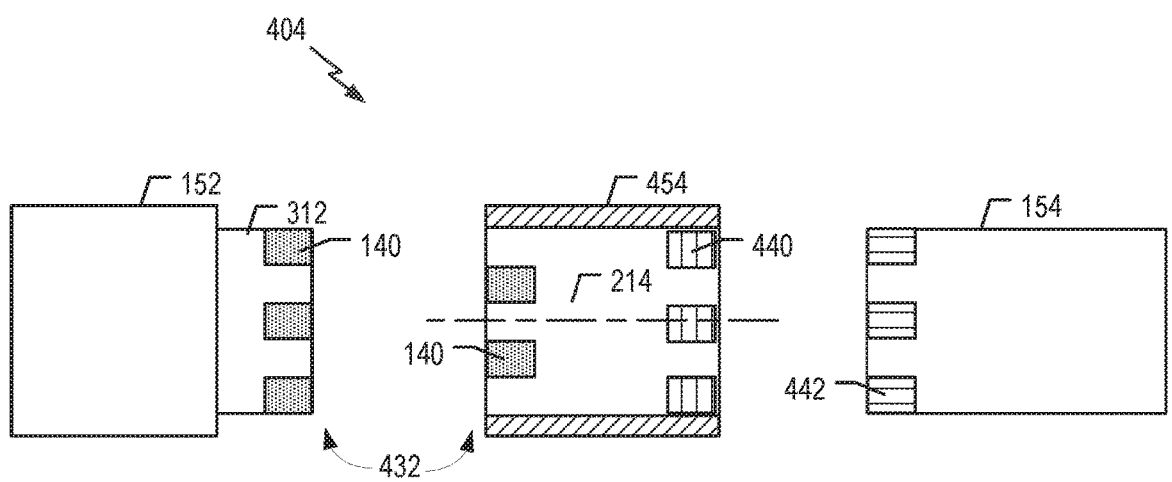
FIG. 4B is side view of an example of a connection point of a system for wound therapy.
Figure 4C:
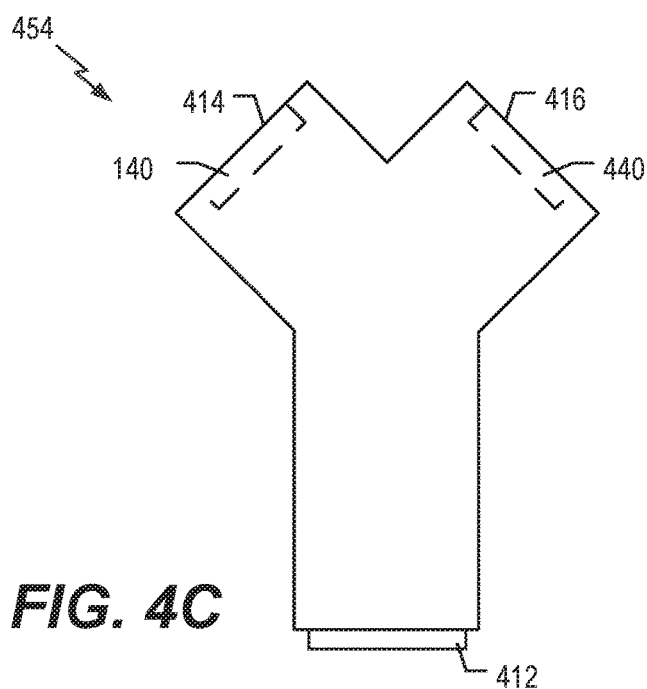
FIG. 4C is side view of an example of a connector of a system for wound therapy.

Referring to FIGS. 2A-2D, 3A-3D, and 4A-4C, each of FIGS. 2A-2D, 3A-3D, 4A and 4B illustrate a side view or a cross-section view of various examples of connection points formed by various arrangements of tubes, connectors, and adhesive, such as LSA 140 and FIG. 4C illustrates a top view of an interconnect (e.g., an inline interconnect) of a connection point. The connection points may include or correspond to the connection points 160-164 of FIG. 1, a connection point between a therapy device and a canister, or the connection points described further herein with reference to FIGS. 5, 6A, 6B, 7A, and 7B. The tubes and connectors may include or correspond to the one or more tubes 114 of FIG. 1, the tubes described further herein with reference to FIGS. 5, 6A, 6B, 7A, and 7B, the connectors 130, 150, 152, 154 of FIG. 1, or the connectors described further herein with reference to FIGS. 5, 6A, 6B, 7A, and 7B. As described herein, the tubes and connectors include one or more lumens. However, for clarity, lumens of the tubes and connectors are not illustrated in FIGS. 2A-2D, 3A-3D, and 4A-4C. Thus, the tubes and connectors illustrated in FIGS. 2A-2D, 3A-3D, and 4A-4C may include additional conduits or through channels to transport fluid and/or light.

Referring to FIGS. 2A-2D, each of FIGS. 2A-2D illustrate a side view or a cross-section view of various examples of connection points formed by insertion ends of tubes and/or connectors. The side view may correspond to exploded side views depicting components of connection points in an unattached or decoupled state and/or be partial or full cross-section views for clarity. FIG. 2A illustrates a side view of an example of a connection point 202, with connector 150 shown in partial cross-section. To illustrate, a bottom half of connector 150 (i.e., below centerline of annular-shaped connector 150) is shown in cross-section. In FIG. 2A, connection point 202 is formed by joining together two connectors, such as connectors 150 and 152. An end of connector 152, i.e., an interface end or portion 212, is inserted into a recess 214 defined by or in a correspond end of connector 150. In some implementations, recess 214 includes or corresponds to a through channel in a connector or a portion of a through channel of the connector. An opposite end of connector 152 may be configured to receive and/or couple to a tube, as illustrated in FIG. 2C. As shown in FIG. 2A, the recess 214 of connector 150 includes LSA 140. To illustrate, interior walls of connector 150 which define recess 214 include LSA 140.

FIG. 2B illustrates a cross-section view of connector 150 of FIG. 2A taken along cross-section line A-A. In FIG. 2B, the recess 214 of the connector 150 is illustrated and the LSA 140 is shown on interior surfaces or walls of connector 150 which define the recess 214. In some implementations, connector 150 is made of a light blocking material. Additionally, or alternatively, an adhesive cover film or layer is positioned over or coupled to LSA 140 to protect LSA 140 from light and/or dust.

Referring to FIG. 2C, a side view of another example of a connection point, connection point 204, having an interconnect 254 (e.g., an in-line tube connector) is shown. In FIG. 2C, connection point 204 is formed by joining connectors 152, 154 with interconnect 254. Interconnect 254 is shown in full-cross section for illustrative purposes in FIGS. 2C and 2D. Interconnect 254 defines multiple recesses 214a and 214b, each recess corresponding to a respective tube or connector. As illustrated in FIG. 2C, interconnect 254 defines a first recess 214a corresponding to connector 152 and defines a second recess 214b corresponding to connector 154. The first recess 214a includes LSA 140 on a portion of the first recess 214a. The second recess 214b includes LSA 140 on an entirety of the second recess 214b. In other implementations, one or more of the recesses 214a, 214b may correspond to a tube and are configured to receive a tube. Additionally, although LSA 140 is applied to a portion of the first recess 214a and an entirety of the second recess 214b, LSA 140 can be applied to one or more of tubes 114 and/or connectors 150, 152, 154 to cover a portion of an entirety of an interface end or portion 212. The first and second recesses 214a, 214b are divided by a center portion 232 of interconnect 254. The center portion 232 may include (e.g., define) one or more channels or lumens to coupled lumens of tube 114a to lumens of connector 154 (and/or of tube 114b).

In some implementations, a connector and/or interconnect may include mechanical alignment devices or features. As illustrated in FIG. 2C, the connector 152 includes a guide pin 222 and interconnect 254 includes a slot 224. The slot 224 is configured to receive the guide pin 222, and when the guide pin 222 is aligned with the slot 224, the connector 152 can be inserted into the interconnect 254. The guide pin 222 and slot 224 may be configured to align components of connectors and/or interconnects. For example, the guide pin 222 and slot 224 may be configured to align one or more lumens (not shown for clarity) of a tube, connector, interconnect, or a combination thereof. In other implementations which couple tube 114a to interconnect 254 (i.e., do not include connector 152), guide pin 222 can be formed on or attached to tube 114a.

In a particular implementation, slot 224 is straight or linear. In such implementations, slot 224 cannot be used as a mechanical connection which allows the connection point to be decoupled and recoupled for further use. Although one guide pin 222 and one slot 224 are illustrated in FIG. 2C, the connector 152 and/or interconnect 254 may have more than one guide pin 222 and slot 224 respectively. In other implementations, slot 224 is curved or has one or more linear sections. For example, slot 224 is a "J" slot or an "L" slot. Such a slot 224 may secure the connection point, but may also enable unintended/undesigned reuse of single-use components. To illustrate, when the guide pin 222 is fully seated in an "L" slot 224, the horizontal portion of the "L" slot 224 does not enable the guide pin 222 to be removed when a force is applied the connector 152 and/or interconnect 254 to disconnect the connection point. To break such a connection point, one of the connector 152 and/or interconnect 254 is twisted to move the guide pin 222 to the vertical portion of the L" slot 224, and then a force is applied the connector 152 and/or interconnect 254 to disconnect the connection point.

In some implementations, tube 114a and connector 152 include an additional connection point. For example, tube 114a and connector 152 may be separate components that are coupled together using a mechanical connection and/or an adhesive, such as LSA 140. In a particular implementation, tube 114a includes LSA 140 on a portion of an exterior wall of tube 114a and/or connector 152 includes LSA 140 on a portion of an interior wall which defines a recess into which tube 114a is inserted, illustrated by dashed lines in FIG. 2C.

FIG. 2D illustrates a side view of another example of a connection point having an interconnect 254, similar to FIG. 2C. However, In FIG. 2D, the connectors 152, 154 include LSA 140 (as opposed to the interconnect 254 including LSA 140). As illustrated in FIG. 2D, external surfaces of connectors 152, 154 have LSA 140 on an interface end or portion 212, i.e., an end which is connected to or inserted into recess 214 of interconnect 254. In FIG. 2D, one or more of connectors 152, 154 may be substituted for tubes, such as tubes 114a or 114b.

In some implementations, a connector or interconnect 254 of a connection point includes a feature or geometry configured to stop a tube or connector from being inserted too far into or through the connector or the interconnect 254. For example, interconnect 254 may include a tapered recess, an internal ridge, a pin, etc., to stop a tube or connector from being inserted too far. As illustrated in FIG. 2D, interconnect 254 includes a ridge 226. Ridge 226 protrudes inward from an interior surface or wall of recess 214 in interconnect 254 to define an aperture that is smaller in diameter than connector 152 (e.g., an exterior diameter thereof) and is configured to control an insertion depth of connector 152 (or tube 114). Additionally, ridge 226 (or another stop feature or element) may subdivide recess 214 into recesses 214a, 214b which corresponds to connectors 152, 154.

In a particular implementation, LSA 140 includes a cover film or layer, such as adhesive cover film 294, as depicted in diagram 290 of FIG. 2B. To illustrate, the adhesive cover film 294 may be attached to LSA 140 to protect LSA 140 from activation, i.e., receiving light and transitioning to the second state, and from dust or contamination. The LSA 140 may be attached to a light blocking layer 292 when material of a component is clear, such as with some implementations of tubes, or may be attached to a light blocking material (e.g., 292) of a component when the component is opaque, such as with connectors made from white or colored plastics. In other implementations, the material of a component includes or corresponds to the light blocking layer 292. For example, the material of a connector may be opaque and block light which would otherwise activate the LSA 140, thus, opaque connectors may not include a separate layer or film to block light (e.g., 292).

FIGS. 3A-3D illustrate side and cross-section views of various examples of connection points formed by mating portions which extend from ends of tubes and/or connectors. Referring to FIG. 3A, a side view of an example of a connection point 302 is shown. In FIG. 3A, connection point 302 is formed by joining together connectors 150 and 152. A mating or interface portion 312 extending from a body (e.g., a connector body) or an end of connector 152, i.e., an interface end, is inserted into a recess 214 in connector 150. As shown in FIG. 3A, the mating or interface portion 312 of connector 152 includes LSA 140. To illustrate, exterior walls of the mating or interface portion 312 of connector 152 include LSA 140.

FIG. 3B illustrates a cross-section view of connector 150 of FIG. 3A taken along cross-section line B-B. In FIG. 3B, the mating portion 312 of the connector 152 is illustrated and the LSA 140 is shown on exterior surfaces or walls of connector 152 which define the mating portion 312. In some implementations, an adhesive cover film or layer (e.g., 294) is positioned over or coupled to LSA 140 to protect LSA 140 from light and/or dust. Additionally, or alternatively, connector 150 is made of a light blocking material (e.g., 292), such that when the optional adhesive cover film (e.g., 294) is removed and connection point 302 is formed, light blocking material (e.g., 292) of connector 150 blocks light from reaching LSA 140.

FIG. 3C illustrates a side view of another example of a connection point, connection point 304, having an interconnect 354. In FIG. 3C, connection point 304 is formed by joining connectors 152, 154 with interconnect 354. Connector 152 is shown in partial cross-section with a bottom half of connector 152 (i.e., below centerline of annular-shaped connector 152) depicting the cross-section of connector 152. Interconnect 354 has or defines multiple mating or interface portions 312a and 312b extending from a body 310 (e.g., a connector body) of interconnect 354, each mating or interface portion corresponding to a recess of a tube or connector. As illustrated in FIG. 3C, interconnect 254 defines a first mating or interface portion 312a corresponding to a first recess 214a of connector 152 and defines a second mating or interface portion 312b corresponding to a second recess 214b of connector 154. The first recess 214a includes LSA 140 on a portion of the first recess 214a, and the second mating or interface portion 312b includes LSA 140 on a portion of the second mating or interface portion 312b. Although mechanical alignment features and stop features are not shown in FIGS. 3A and 3C, connection points 302 and 204 may include mechanical alignment features and/or stop features, as described with reference to FIGS. 2C and 2D and illustrated in FIG. 3D.

FIG. 3D illustrates a side view of another example of a connection point, connection point 306, having an interconnect 354. Interconnect 354 is shown in full cross-section for illustrative purposes in FIG. 3D. In FIG. 3D, connection point 306 is formed by joining connectors 152, 154 with interconnect 354. To illustrate, connectors 152, 154 each have a correspond mating portion 312a, 312b. Mating portion 312a is inserted into correspond recess 214a of interconnect 354, and mating portion 312b is inserted into correspond recess 214b of interconnect 354. As illustrated in FIG. 3D, LSA 140 is provided on interconnect 354 in recess 214a and provided on connector 154 on mating portion 312b. In other implementations, LSA 140 may be provided on other surfaces of components of connection point 306, as described herein.

Referring to FIGS. 4A-C, FIGS. 4A and 4B illustrate side views of various examples of connection points including elements of FIGS. 2A-2D and 3A-3D. FIG. 4C illustrates a top view of an interconnect 454 having multiple inlet or outlet ports. Referring to FIG. 4A, a side view of another example of a connection point 402 is shown. In FIG. 4A, connection point 402 includes an interconnect 454, tubes 114a, 114b. Tube 114b (or alternatively connector 154) is shown in partial cross-section with a bottom half of tube 114b (i.e., below centerline of annular-shaped tube 114b) depicting the cross-section of tube 114b. Interconnect 454 includes both a recess 214 configured to receive a tube or connector and a mating portion 312 portion extending from a base of interconnect 454 which is configured to be inserted into a recess of a tube, a connector, or another component. FIG. 4A illustrates one exemplary configuration of LSA 140 for connection point 402 where interconnect 454 does not have LSA 140, i.e., LSA 140 is provided in a 212 of tube 114a (or connector 152) and in a recess of tube 114b. In other implementations, recess 214, mating portion 312, or both, of interconnect 454 have LSA 140.

FIG. 4B illustrates a side view of another example of a connection point including interconnect 454. Interconnect 454 is shown in full cross-section for illustrative purposes in FIG. 4B. In FIG. 4B, connection point 404 is formed using a pattern 432 of LSA 140 and a two-part LSA 140. Two-part LSA 140 includes a first part 440 and a second part 442. As illustrated in FIG. 4B, interconnect 454 defines a recess 214 which is configured to receive connectors 152, 154. Connector 152 and interconnect 454 each include a pattern 432 of LSA 140, i.e., one or more portions of LSA 140. Connector 154 and interconnect 454 each include portions of parts 440, 442 of two-part LSA 140. As illustrated in FIG. 4B, interconnect 454 includes portions of a first part 440 of two-part LSA 140, and connector 154 includes portions of a second part 440 of two-part LSA 140. The pattern 432 and portions of parts 440, 442 may be designed such that they align to form a bond.

In some implementations, a mechanical guide feature, such as pin 222 and slot 224 is used to align the LSA 140, parts 440 and 442 of LSA 140, or elements (e.g., lumens) of the connection point components (e.g., connectors and/or tubes). Aligning the LSA 140 includes aligning a pattern 432 of LSA 140, aligning parts 440, 442 of a two-part LSA 140, or both. Additionally, or alternatively, mechanical stop features can be used to control insertion depth to align the LSA 140 and/or parts 440 and 442 of two-part LSA 140. As illustrated in FIG. 4B, LSA 140 is aligned such that one or more portions of LSA 140 do not overlap, and such that portions of parts 440 and 442 overlap. Although FIG. 4B illustrates a pattern 432 of LSA 140 and a two-part LSA 140, other implementations described herein may use patterns of LSA 140, two-part LSAs 140, or both. Additionally, or alternatively, the two-part LSA 140 may be used without a pattern.

FIG. 4C illustrates a top view of an example of interconnect 454 with multiple connection ports on an inlet or outlet side. As illustrated in FIG. 4C, the interconnect 454 is a "Y" interconnect. In other implementations, other shapes may be used, such as a "T" interconnect. Interconnect 454 is configured to be coupled with corresponding a tube or connector for each port. The interconnect 454 may be connected to the tubes and/or or connectors by any of the above disclosed examples. As illustrated in the example of FIG. 4C, interconnect 454 is configured be inserted into a tube or a connector at a first port 412 and is configured to receive a respective tube or connector at second and third ports 414 and 416. For example, first port 412 may have a mating portion 312, and second and third ports 414 and 416 may each have recesses, such as a recess 214. LSA 140 may be provided on one or more of interconnect 454, components coupled to interconnect 454, or a combination thereof. As a particular illustrative, non-limiting example, interconnect 454 does not include LSA 140.

Additionally, when an interconnect is used, such as interconnect 254, 354, 454, one or more connections thereof may employ different LSAs 140, such as UV and/or visible light LSAs. In such implementations, a particular connection or connections of a connection point may be disconnected, such as inlet side only connections, outlet side only connections, or a portion of connections of a side (inlet or outlet). As an illustrative, non-limiting example, interconnect 454 may have a first type of LSA 140 (e.g., UV LSA) associated with second port 414 and a second type of LSA 440 (e.g., visible light LSA) associated with third port 416. In such implementations, the LSA 140 and LSA 440 may be provided on the interconnect 454 or on a component which is coupled to the interconnect 454, such as a tube or a connector described herein.

As illustrated in FIGS. 2A-2D, 3A-3D, and 4A-4C, a connection point can be formed in various different ways. Although a connection point of FIGS. 2A-2D, 3A-3D, and 4A-4C is illustrated with particular components and a particular configuration, the components and/or configuration may be modified in other implementations. For example, although FIG. 2A includes connectors 150 and 152, in other implementations connection point 202 is formed from one or more tubes (e.g., tube 114a and/or tube 114b), one or more connectors (e.g., 130, 150, 152, 154), interconnects, or a combination thereof. Additionally, elements or configurations of the components of the connection point examples described with reference to FIGS. 2A-2D, 3A-3D, and 4A-4C may be combined with each other. For example, one or more of the mechanical guide features of FIG. 2C, 2D, or 3C may be combined with the two-part LSA 140 of FIG. 4B, the pattern 432 of LSA 140 of FIG. 4B, or both.

In a particular implementation, a tube connector (e.g., 130, 150, 152, 154, 254, 354, 454) for system 100 includes a connector body (e.g., 310) configured to define a mating portion (e.g., 212, 312) and LSA 140 coupled to the mating portion of the connector body. The mating portion is configured to mate with a corresponding mating portion (e.g., 214) of a tube (e.g., 114, 614, 714).

In a particular implementation, a tube (e.g., 114a, 114b) for system 100 includes a body (e.g., exterior walls) configured to define at least one lumen (e.g., 621, 721-728) and LSA 140 coupled to a mating portion (e.g., 212, 312) of the body.

FIG. 5 illustrates a schematic cross-section view of an example of a dressing of a therapy system, such as dressing 116 of system 100. In FIG. 5, dressing 116 includes LSA 140 for adhesive 502 and defines an optical path to transport light received from connector 130 of dressing 116 to LSA 140 of adhesive 502. For example, dressing 116 defines an aperture or cavity 504 or includes a light passing material or medium that is configured to transport and diffuse received light to adhesive 502. Cavity 504 (or light passing medium) is configured to pass (e.g., transport and/or diffuse) received light to switch the LSA 140. Adhesive 502 may include or correspond to adhesive 137 of FIG. 1. As illustrated in FIG. 5, drape 132 of dressing 116 receives light from tube 114b via an aperture 512 (or light passing medium) in connector 130, and cavity 504 transports the received light to LSA 140 on adhesive 502. To illustrate, light reflects off walls of the cavity 504 near the connector 130 and travels to peripheral portions of cavity 504 and dressing 116 where the light diffuses into adhesive 502 to activate LSA 140.

After therapy is complete or a component has reached end of life, light is directed to the LSA 140. In the example of FIG. 5, when dressing 116 is to be removed, such as after therapy is completed or dressing 116 is due to be changed, a UV light source is activated and UV light travels to dressing 116 via tube 114b. For example, UV light source (e.g., UV device 118) is included in a therapy device and/or a container, such as therapy device 110 and/or canister 112 of FIG. 1. As another example, UV light source, such as second light device 518, is separate from the canister and/or the therapy system, and the second light device 518 is coupled to a port or window of a connector or a tube to provide the UV light to dressing 116 via tube 114b. The second light device 518 may include or correspond to UV device 118, as described herein.

In other implementations, dressing 116 receives the UV light directly from a UV light source or from ambient light. In some such implementations, drape 132 of dressing 116 includes a shroud 524. The shroud 524 is positioned such that the shroud blocks the LSA 140 from receiving light, such as ambient light. The shroud 524 is formed of or includes a material that is configured to block (e.g., reflect or absorb) ambient light that would otherwise activate LSA 140. Thus, shroud 524 enables the use of ambient light and/or does not require a dedicated light device, transporting light via components of a therapy system, or both. Accordingly, LSA 140 can be activated without a dedicated light device and the connection points can be disconnected without the dedicated light device. In other such implementations, dressing 116 includes a port or window 522 configured to receive or be coupled with a light source, such as UV device 118. To illustrate, connector 130 or drape 132 includes a port 522 that is optically coupled to or in optical communication with cavity 504. In a particular implementation, the port 522 (or window) includes a removable cover or film that blocks light from entering the cavity 504 and traveling to the LSA 140 of adhesive 502. To illustrate, port 522 (or window) may pass or propagate light to cavity 504 to diffuse to the LSA 140 of adhesive 502. Thus, port or window 522 enables the use of ambient light and/or does not require a dedicated light device, transporting light via components of a therapy system, or both. Accordingly, LSA 140 can be activated without a dedicated light device and the connection points can be disconnected without the dedicated light device.

Figures 6A, 6B:
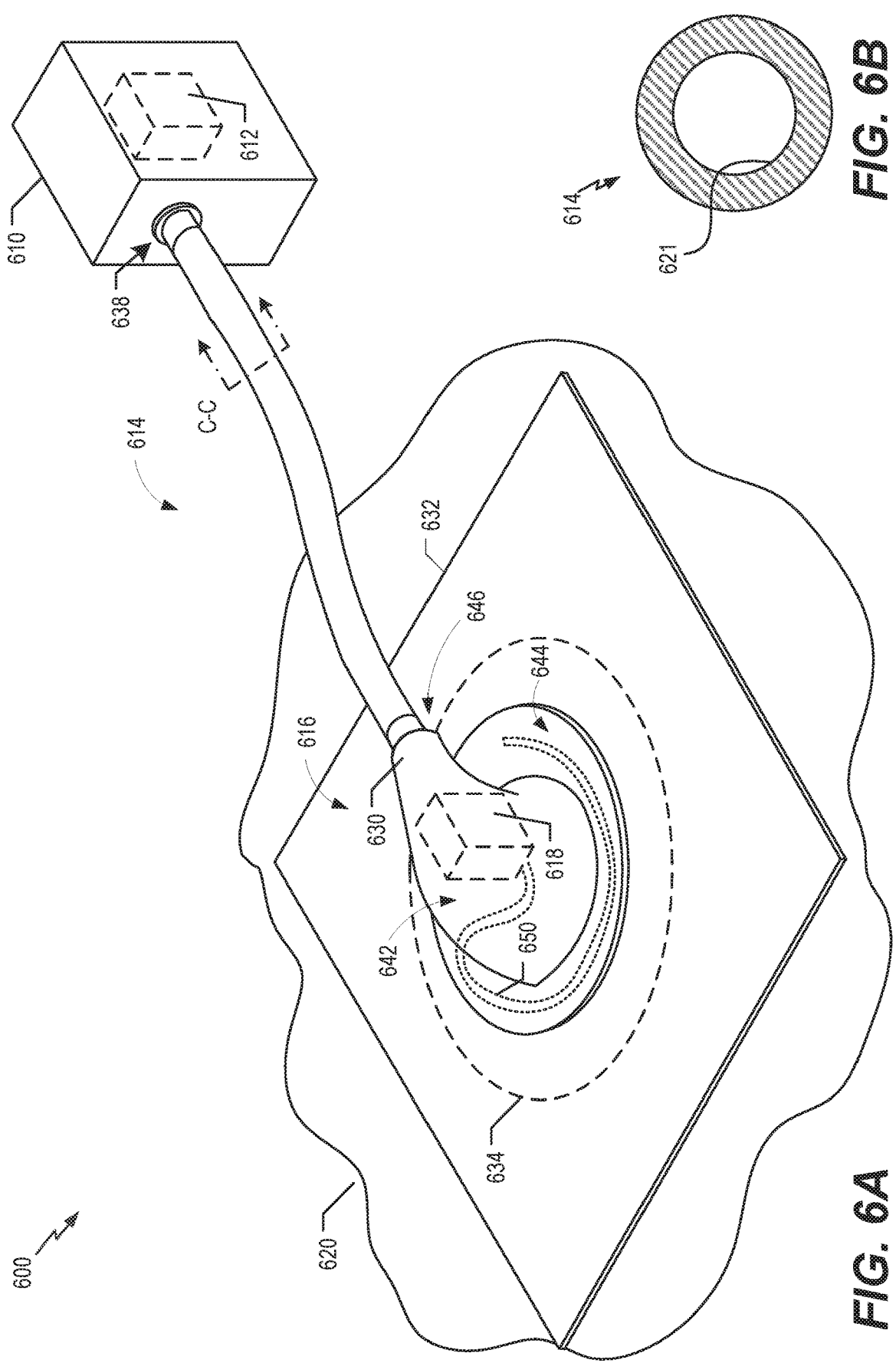
FIG. 6A is a perspective view of an example of a system for wound therapy.
FIG. 6B is a cross-sectional view of an example of a tube taken along line C-C of FIG. 6A.

In alternative implementations, dressing 116 includes an internal tube (e.g., fiber optic tube) configured to transport received light to the adhesive, as described further with reference to FIG. 6A. In some such implementations, the internal tube has a high refractive index along a length of the internal tube and has a relatively lower refractive index at an end of the tube to permit light to escape from the tube.

In some implementations, a cover film (e.g., 294) is attached to the adhesive 502. The cover film may be formed of a thin, clear, flexible, breathable material with a high refractive index. One exemplary material for the cover film is polyurethane (PU). In a particular implementation, in areas where the adhesive 502 abuts the layer (e.g., a diffuser layer), the cavity 504 or light passing medium has a relatively lower refractive index to allow light that reaches the diffuser layer to reflect/refract and be distributed over the diffuser layer. The diffuser layer can emit a larger portion of the light in an area of the diffuser layer with a low refractive index.

In some implementations, a sheath 514 of high refractive material is coupled to at least one tube of the system, such as 114b. For example, the sheath 514 is formed with the tube 114b or is coupled to the tube 114b after the system 100 is connected (e.g., during or after operation). The sheath 514 is configured to refract light within the tubes 114 and prevent or reduces light within the tubes 114 from escaping the tubes 114. To illustrate, sheath 514 refracts light (a portion thereof) that has escaped the tube 114b back into the tube 114b. Additionally or alternatively, the tube, such as tube 514b, or one or more lumens thereof may include a coating of high refractive material, as described herein. In some implementations, at least one tube of the system (e.g., a tube which includes sheath 514) includes or is made from a low refractive material, such as a material with a refractive index that is less than 1.6. In a particular implementation, low refractive material has a refractive index less than or equal to 1.5. Thus, providing a sheath 514 on a tube (or one or more lumens thereof) improves propagation of light along the tube and enables the UV device to use less power and/or use of a smaller UV device.

FIG. 6A shows a perspective view of an illustrative system 600 (e.g., a hyperbaric oxygen therapy system) for oxygen therapy using positive-pressure. System 600 may include a therapy device 610, canister 612, a tube 614, a dressing 616, and a UV device 618. System 600 is configured to provide oxygen and positive-pressure at a tissue site 620 associated with a target area of a patient. For example, dressing 616 may be in fluid communication with tissue site 620 and may be in fluid communication with therapy device 610 via tube 614. Device 610 and dressing 616 may include or correspond to device 110 and dressing 116, respectively. Canister 612 and tube 614 may include or correspond to canister 112 and one or more tubes 114 (e.g., tube 114a, 114b), respectively. In some implementations, system 600 may include one or more components commercially available through and/or from KCI USA, Inc. of San Antonio, Tex., U.S.A., and/or its subsidiary and related companies (collectively, "KCI").

System 600 includes one or more connection points (e.g., interfaces). For example, system 600 may include a connection point between components (e.g., 610-618) of system 600, between subcomponents of a component, or between a component of system 600 and tissue site 620. Additionally, at least one connection point is formed using LSA 140.

Therapy device 610 (e.g., a positive-pressure treatment apparatus) is configured to provide oxygen at a positive-pressure via tube 614 and dressing 616. For example, therapy device 610 may include a positive-pressure source, such as a pressurized oxygen container, an oxygen concentrator, or an oxygen collector (e.g., a pump and a filter) and/or the like, configured to be actuatable (and/or actuated) to apply positive-pressure (e.g., hyperbaric pressure) to dressing 616. In other implementations, positive-pressure source is included in dressing 616 that includes connector 630, or positive-pressure source is external to dressing 616, included in connector 630, and coupled to dressing 616 via connector 630. As illustrative, non-limiting examples, positive-pressure applied to a tissue site may typically ranges between 5 millimeters mercury (mm Hg) (667 pascals (Pa)) and 30 mm Hg (4.00 kilo (k) Pa). Common therapeutic ranges are between 10 mm Hg (1.33 kPa) and 25 mm Hg (3.33 kPa).

In some implementations, as described further with reference to FIG. 7A, the therapy device 610 includes a reduced-pressure source, such as a vacuum source (e.g., a pump and/or the like), configured to be actuatable (and/or actuated) to apply reduced-pressure (e.g., negative pressure) to the dressing 616. In such implementations, therapy device 610 may alternate between providing positive-pressure therapy and negative-pressure therapy to the dressing 616, may provide positive-pressure therapy to a first portion of the dressing 616 and negative-pressure therapy to a second portion of the dressing 616, may provide no positive or negative pressure, or a combination thereof. In some such implementations, the therapy device 610 can provide positive-pressure therapy and negative-pressure therapy to the dressing 616 at the same time (e.g., partially concurrently). As illustrative, non-limiting examples, reduced-pressure applied to a tissue site may typically ranges between -5 millimeters mercury (mm Hg) (-667 pascals (Pa)) and -500 mm Hg (−66.7 kilo (k) Pa). Common therapeutic ranges are between −75 mm Hg (−9.9 kPa) and −300 mm Hg (−39.9 kPa).

As illustrated in FIG. 6A, therapy device 610 includes canister 612 to receive fluid from tissue site 620 or to provide fluid to tissue site 620. Although canister 612 is illustrated as being internal to and/or integrated with therapy device 610, in other implementations, canister 612 is external to therapy device 610, as illustrated and described with reference to FIG. 1. Canister 612 may include or correspond to canister 112 of FIG. 1.

Therapy device 610 may also include one or more other components, such as a sensor, a processing unit (e.g., a processor), an alarm indicator, a memory, a database, software, a display device, a user interface, a regulator, and/or another component, that further facilitate positive-pressure therapy. Additionally, or alternatively, therapy device 610 may be configured to receive fluid, exudate, and or the like via dressing 616 and tube 614. Therapy device 610 may include one or connectors, such as a representative connector 638 (e.g., 150). Connector 630 is configured to be coupled to tube 614. Additionally, or alternatively, therapy device 610 may include one or more sensors, such a pressure sensor (e.g., a pressure transducer). The one or more sensors may be configured to enable therapy device 610 to monitor and/or sense a pressure associated with tube 614 and/or dressing 616. An illustrative example of therapy device 610 is described further herein at least with reference to FIG. 7A.

Tube 614 includes one or more lumens (e.g., one or more through conduits), such as a single lumen conduit or multiple single-lumen conduits. Tube 614 (e.g., a least one of the one or more lumens) is configured to enable fluid communication between therapy device 610 and dressing 616. For example, fluid(s) and/or exudate can be communicated between therapy device 610 and dressing 616, and/or one or more pressure differentials (e.g., positive-pressure, negative pressure, or both) can be applied by therapy device 610 to dressing 616. As an illustrative, non-limiting illustration, tube 614 is configured to deliver at least pressurized oxygen from therapy device 610 to dressing 616 to establish positive-pressure. Communication of fluid(s) and application of a pressure differential can occur separately and/or concurrently.

In some implementations, tube 614 may include multiple lumens, such as a primary lumen (e.g., a positive-pressure/fluid lumen) for application of positive-pressure and/or communication of fluid, and one or more secondary lumens proximate to or around the primary lumen. The one or more secondary lumens (e.g., one or more ancillary/peripheral lumens) may be coupled to one or more sensors (of therapy device 610), coupled to one or more valves, as an illustrative, non-limiting example. Although tube 614 is described as a single tube, in other implementations, system 600 may include multiple tubes, such as multiple distinct tubes coupled to therapy device 610, dressing 616, or both.

Referring to FIG. 6B, an illustrative example of a cross-section of tube 614 (in which tube 614 comprises a single lumen) along line C-C of FIG. 6A is shown. Tube 614 may include a primary lumen 621 (e.g., a positive-pressure/fluid lumen). In other implementations, tube 614 may include one or more secondary lumens, such as a negative-pressure/fluid lumen, one or more sense lumens, etc., or a combination thereof, such as described with reference to at least FIG. 7B. Although tube 614 has been described and/or shown as having a circular cross-sectional shape, in other implementations, tube 614 may have a cross-sectional shape other than a circle, such as an oval, triangle, quadrilateral, pentagon, star, or another shape, as illustrative, non-limiting examples.

Referring to FIG. 6A, dressing 616 includes a connector 630 (also referred to as a dressing connection pad or a pad), a drape 632, and a manifold 634 (also referred to as a distribution manifold or an insert). Drape 632 may be coupled to connector 630. To illustrate, drape 632 may be coupled to connector 630 via an adhesive, a separate adhesive drape over at least a portion of connector 630 and at least a portion of drape 632, or a combination thereof, as illustrative, non-limiting examples.

Drape 632 may be configured to couple dressing 616 at tissue site 620 and/or to provide a seal to create an enclosed space (e.g., an interior volume) corresponding to tissue site 620. For example, drape 632 may be configured to provide a fluid seal between two components and/or two environments, such as between a sealed therapeutic environment and a local ambient environment. To illustrate, when coupled to tissue site 620, drape 632 is configured to maintain a pressure differential (provided by a positive-pressure source 678 or a negative-pressure source) at tissue site 620. Drape 632 may include a drape aperture that extends through drape 632 to enable fluid communication between device and target tissue, as describe further with reference to FIG. 7A. Drape 632 may be configured to be coupled to tissue site 620 via an adhesive, such as a medically acceptable, pressure-sensitive adhesive that extends about a periphery, a portion, or an entirety of drape 632. Additionally, or alternatively, drape 632 may be coupled to tissue site 620 via a double-sided drape tape, paste, hydrocolloid, hydrogel, and/or other sealing device or element, as illustrative, non-limiting examples.

Drape 632 may include an impermeable or semi-permeable, elastomeric material, as an illustrative, non-limiting example. In some implementations, drape 632 may be liquid/gas (e.g., moisture/vapor) impermeable or semi-permeable. "Elastomeric" means having the properties of an elastomer. For example, elastomer generally refers to a polymeric material that may have rubber-like properties. More specifically, an elastomer may typically have ultimate elongations greater than or equal to 100% and a significant amount of resilience. The resilience of a material refers to the material's ability to recover from an elastic deformation. Elastomers that are relatively less resilient may also be used as these elastomers. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. In some implementations, drape 632 may include the "V.A.C.® Drape" commercially available from KCI. Additional, specific non-limiting examples of materials of drape 632 may include a silicone drape, 3M Tegaderm® drape, and a polyurethane (PU) drape such as one available from Avery Dennison Corporation of Pasadena, Calif. An additional, specific non-limiting example of a material of the drape 632 may include a 30 micrometers (μm) matt polyurethane film such as the Inspire™ 2317 manufactured by Exopack™ Advanced Coatings of Matthews, N.C.

Manifold 634 is configured to be positioned on and/or near tissue site 620, and may be secured at the tissue site 620, such as secured by drape 632. The term "manifold" as used herein generally refers to a substance or structure that may be provided to assist in applying a pressure differential (e.g., positive-pressure differential) to, delivering fluids to, or removing fluids and/or exudate from a tissue site and/or target tissue. The manifold typically includes a plurality of flow channels or pathways that distribute fluids provided to and removed from the tissue site. In an illustrative implementation, the flow channels or pathways are interconnected to improve distribution of fluids provided to or removed from the tissue site. Manifold 634 may be a biocompatible material that may be capable of being placed in contact with the tissue site and distributing positive and/or negative-pressure to the tissue site. Manifold 634 may include, without limitation, devices that have structural elements arranged to form flow channels, such as foam, cellular foam, open-cell foam, porous tissue collections, liquids, gels, and/or a foam that includes, or cures to include, flow channels, as illustrative, non-limiting examples. Additionally, or alternatively, manifold may include polyethylene, a polyolefin, a polyether, polyurethane, a co-polyester, a copolymer thereof, a combination thereof, or a blend thereof.

In some implementations, manifold 634 is porous and may be made from foam, gauze, felted mat, or other material suited to a particular biological application. In a particular implementation, manifold 634 may be a porous foam and may include a plurality of interconnected cells or pores that act as flow channels. The foam (e.g., foam material) may be either hydrophobic or hydrophilic. As an illustrative, non-limiting example, the porous foam may be a polyurethane, open-cell, reticulated foam such as GranuFoam® material manufactured by Kinetic Concepts, Incorporated of San Antonio, Tex.

In some implementations, manifold 634 is also used to distribute fluids such as medications, antibacterials, growth factors, and other solutions to the tissue site. Other layers may be included in or on manifold 634, such as absorptive materials, wicking materials, hydrophobic materials, and hydrophilic materials. In an implementation in which the manifold 634 includes a hydrophilic material, manifold 634 may be configured to wick fluid away from tissue site 620 and to distribute positive-pressure to tissue site 620. The wicking properties of manifold 634 may draw fluid away from the tissue site 620 by capillary flow or other wicking mechanisms. An illustrative, non-limiting example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether and/or foams that have been treated or coated to provide hydrophilicity.

In some implementations, manifold 634 is constructed from bioresorbable materials that do not have to be removed from tissue site 620 following use of the system 600. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 634 may further serve as a scaffold for new cell-growth, or a scaffold material may be used in conjunction with manifold 634 to promote cell-growth. A scaffold may be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. Although a manifold 634 is illustrated in FIG. 6A, in other implementations, dressing 616 does not include manifold 634. In such implementations, drape 632 of dressing 616 is coupled to connector 630.

Connector 630 includes a body 642 (e.g., housing) and a base 644, and is configured to be coupled to tube 614 via an interface 646 (e.g., a port). Base 644 is configured to be coupled to dressing 616. For example, base 644 may be coupled, such as via an adhesive, to drape 632 and/or manifold 634. In some implementations, base 644 comprises a flange that is coupled to an end of body 642 and/or is integrally formed with body 642. Connector 630, such as body 642, base 644, interface 646, or a combination thereof, may be made of rigid material and/or a semi-rigid material. In a non-limiting example, connector 630 may be made from a plasticized polyvinyl chloride (PVC), polyurethane, cyclic olefin copolymer elastomer, thermoplastic elastomer, poly acrylic, silicone polymer, or polyether block amide copolymer. In some implementations, connector 630 is formed of a semi-rigid material that is configured to expand when under a force, such as positive-pressure greater than or equal to a particular amount of pressure. Additionally or alternatively, connector 630 may be formed of a semi-rigid material that is configured to collapse when under a force, such as reduced-pressure less than or equal to a threshold pressure.

Body 642 includes one or more channels or one or more conduits that extend from and/or are coupled to interface 646. To illustrate, body 642 may include a primary channel configured to be coupled in fluid communication with a primary lumen (e.g., 621) of tube 614. The primary channel may be coupled to a cavity (e.g., a tissue cavity partially defined by body 642) having an aperture open towards manifold 634 (and/or towards tissue site 620). For example, the primary channel may include a first opening associated with interface 646 and a second opening (distinct from the aperture of the cavity) associated with the cavity. Thus, the primary channel may define a through channel of body 642 to enable fluid communication between interface 646 and tissue site 620.

Body 642 includes a channel (e.g., a through channel) having a first aperture open opposite dressing 616 and a second aperture open towards dressing 616. For example, the first aperture is located on an outer surface side (e.g., an ambient environment surface) of connector 630 and the second aperture is located on an inner surface side (e.g., a tissue facing side) of connector 630. The second aperture is configured to be coupled to one or more lumens of tube 614, such as coupled via the cavity.

Connector 630 includes UV device 618 or is configured to receive UV device 618 (e.g., includes a port for insertion of UV device 618). As illustrated in FIG. 6A, UV device 618 is incorporated into body 642 of connector 630. For example, UV device 618 may be incorporated in the through channel and configured to emit light through the first aperture, the second aperture, or both. To illustrate, UV device 618, alone or in combination with one or more reflectors, refractors, collimators, lens, waveguides, etc., directs light into the tubes 614 (a first tube (e.g., 114a), a second tube (e.g., 114b), a third tube, etc.) via the first aperture and directs light to a light guide 650 via the second aperture.

Light guide 650 (e.g., a wave guide) is incorporated into connector 630 and may include one or more components configured to transport light from UV device 618 to LSA (not shown, such as adhesive 137, 502) attached to drape 632. As illustrated in FIG. 6A, light guide 650 is an optical tube or lumen incorporated into body 642 and base 644 and configured to deliver light to drape 632 (e.g., a cavity thereof, such as cavity 504) and/or adhesive (137, 502) attached thereto. Additionally, or alternatively, light guide 650 is incorporated into drape 632. In a particular implementation, light guide 650 is a fiber optic cable. Light guide

650 may include one or more lumens to transport the light. For example, light guide 650 may include one lumen for each adhesive or portion/section of adhesive. As another example, a single light guide 650 having a single lumen transports the light, and apertures or high refractive/transmission material (e.g., diffusion material) is incorporated into light guide 650 to form a plurality of transmission elements such that light guide 650 disperses or diffuses light through the single lumen into drape 632 and/or adhesive via the plurality of transmission elements.

Although light guide 650 is illustrated in FIG. 6 along with a UV device 618 incorporated into connector 630, other implementations described herein can incorporate a light guide, such as light guide 650, within dressing 116 to transport/deliver light to LSA. To illustrate, in implementations where a UV device is incorporated into device 610 or is delivered to dressing 616 via one or more tubes and connector 630, light guide 650 may be coupled to connector 630 to receive the light and to transport and deliver the light to the adhesive which couples the dressing 116 to the tissue site 620. Illustrative, non-limiting examples of commercially available connectors include a "V.A.C. T.R.A.C.® Pad," or "Sensa T.R.A.C.® Pad" available from Kinetic Concepts, Inc. (KCI) of San Antonio, Tex.

During operation of system 600, dressing 616 is coupled to tissue site 620. Additionally, dressing 616 is coupled to device 610 via tube 614. Positive-pressure can be generated and/or applied to dressing 616 (e.g., an interior volume of dressing 616) by a positive-pressure source 678 associated with device 610. When positive-pressure is generated and/or applied to dressing 616, fluid or medication from device 610, such as from canister 612, may be transported to dressing 616. Furthermore, in some implementations, reduced-pressure can be applied to dressing 616 (e.g., the interior volume of dressing 616 or a second interior volume of the dressing 616) by a reduced-pressure source associated with device 610. When reduced-pressure is applied to dressing 616 (e.g., when vacuum pressure is generated, fluid, exudate, or other material within dressing 616 may be transported to canister 612 of device 610.

After operation or when replacing a component of system 600, UV device 618 may be activated to provide UV light to dressing 116, and optionally connection points between other components of system 600. To illustrate, UV device 618 emits UV light into light guide 650. Light guide 650 receives the UV light and transports the UV light through body 642 and base 644 to drape 632, manifold 634, adhesive attached to dressing 116, or a combination thereof. In a particular implementation, light guide 650 delivers light to drape 632 via a plurality of transmission elements along a length of light guide 650. Drape 632 receives the light and diffuses (or further diffusers the light) to deliver the light to adhesive which coupled drape 632 to tissue site 620. The UV light causes the LSA to transition from the first state to the second state and facilitates easy pain and trauma free removal of adhesive and dressing 616 from tissue site 620.

In alternative implementations, dressing 616 is configured to receive UV device 618 (distinct UV device separate from dressing 616). For example, dressing 616 includes a port (e.g., 522) configured to couple (e.g., optically couple) UV device 618 to light guide 650. As another example, dressing 616 includes one or more windows (e.g., 522) which enable UV light generate by UV device 618 to pass through to LSA or light guide 650. The one or more windows may be protected by a cover film or shroud (e.g., 524) when the UV device 618 is not in use.

In a particular implementation, a dressing 616 for system 600 includes a connector body 642 configured to receive light, LSA 140 coupled to the dressing 616, and a drape 632 coupled to the connector body 642 and including an optical channel (e.g., cavity 504 or light guide 650) configured to receive the light from the connector body 642 and provide the light to the LSA 140.

In a particular implementation, system 100 includes a canister 618 which includes a connection port 522 configured to couple to a connector (e.g., 150) or a tube (e.g., 614), and a canister body including light transmission means (e.g., 142) for passing light and providing the light to the connection port 522.

Thus, a UV device can be separate from a therapy device and/or incorporated in a dressing of a system including LSA connection points to provide secure single-use connections and to hinder or prevent reuse of single-use components to reduce infection and contamination. Additionally, system 100 (e.g., one or more of the components thereof) configured to provide easy assembly and disconnection with a low disconnection force enabling the young, elderly, and sick to easily connect and disconnect the devices and systems.

Referring to FIG. 7A, an illustrative example of an illustrative system 700 (e.g., a pressure therapy system) is shown. System 700 includes a pressure therapy device 710 (e.g., a positive-pressure or a negative-pressure therapy apparatus), a tube 714, and a dressing 716. Dressing 716 is coupled to device 710 via one or more tubes 714. Device 710 and dressing 716 may include or correspond to device 110 or device 610 and dressing 616, respectively. One or more tubes 714 may include or correspond to tube(s) 114 or tube(s) 614.

System 700 includes one or more connection points (e.g., interfaces). For example, system 700 may include a connection point between components of system 700, between subcomponents of a component, or between a component of system 700 and tissue site 720. Additionally, at least one connection point is formed using LSA 140.

Referring to FIG. 7B, an illustrative example of a cross-section of tube 714 (when tube 114 comprises multiple lumens) along line D-D of FIG. 7A is shown. Tube 714 may include a primary lumen 721 (e.g., a positive-pressure/fluid lumen) and one or more secondary lumens, such as a first secondary lumen 722 (e.g., a negative-pressure/fluid lumen), a second secondary lumen 724 (e.g., a waveguide lumen), a third secondary lumen 726 (e.g., a sense lumen), and a fourth secondary lumen 728 (e.g., a second sense lumen). Although described as having a single primary lumen (e.g., 721), tube 714 may have multiple primary lumens, such as a first primary lumen for positive pressure and a second primary lumen for transporting light or for negative-pressure. Additionally, or alternatively, primary lumen 721 may be configured to for both positive-pressure and negative-pressure. Although described as having four secondary lumens, in other implementations, tube 714 may include fewer than or more than four secondary lumens. Although tube 714 has been described and/or shown as having a circular cross-sectional shape, in other implementations, tube 714 may have a cross-sectional shape other than a circle, such as an oval, triangle, quadrilateral, pentagon, star, or another shape, as illustrative, non-limiting examples. In an alternative implementation, primary lumen 721 may be a negative-pressure/fluid lumen, first secondary lumen 722 may be a positive-pressure/fluid lumen), and secondary lumens 724, 726, 728 may be waveguide or sense lumens.

Dressing 716 is configured to be coupled to (e.g., adhered to) a tissue site 720 of a patient. Tissue site 720 may include or correspond to tissue site 120 or tissue site 620. Dressing 716 may include one or more components, such as a connector 730, a drape 732, a manifold 734, or a combination thereof, as illustrative, non-limiting examples. Connector 730 may include or correspond to connector 130. Drape 732 and manifold 734 may include or correspond to drape 132 and manifold 134, respectively. Drape 732 may be coupled to connector 730 and/or manifold 734, and may include an opening 735 (e.g., a drape aperture) to enable communication (e.g., fluid communication) between connector 730 and manifold 734.

As shown, drape 732 is coupled to tissue site 720 via a representative adhesive 737, such as a medically acceptable, pressure-sensitive adhesive that extends about a periphery, a portion, or an entirety of drape 132. Additionally, or alternatively, drape 732 may be coupled to tissue site 720 via a double-sided drape tape, paste, hydrocolloid, hydrogel, and/or other sealing device or element, as illustrative, non-limiting examples. Drape 732 is configured to be coupled to tissue site 720 such that drape 732 covers manifold 734 (and target tissue 736) to form and/or define an interior volume 738 between drape 732 and tissue site 720 (e.g., target tissue 736). To illustrate, interior volume 738 may correspond to a sealed therapeutic environment. For example, the tissue proximate the target tissue 736 may be undamaged epidermis peripheral to target tissue 736. The sealed therapeutic environment may be isolated from an external environment, such as an external environment at ambient pressure.

As shown, manifold 734 is positioned within interior volume 738 at (e.g., on or above) target tissue 736 of tissue site 720. In some implementations, manifold 734 may contact tissue site 720, target tissue 736, or both. In some implementations, such as when target tissue 736 extends into tissue from a tissue surface 719 creating a cavity, manifold 734 may partially or completely fill the cavity. In other implementations, manifold 734 may be placed over target tissue 736. Manifold 734 may take one or more forms, and/or may have one or more configurations (e.g., sizes, shapes, and/or thicknesses), depending on one or more factors, such as the type of treatment being implemented, the nature and size of target tissue 736, a stage of treatment, or a combination thereof. For example, the size and shape of the manifold 734 may be adapted to target tissue 736 and/or tissue site 720. To illustrate, manifold 734 may be adapted to a contours of target tissue 736 and/or tissue site 720. In a particular implementation, manifold 734 includes a foam, such as GranuFoam® material manufactured by Kinetic Concepts, Incorporated of San Antonio, TX, as an illustrative, non-limiting example.

Connector 730 may include a connector body 742, a base 744, and an interface 746 (e.g., a port). Connector body 742 (e.g., a housing) may include or correspond to body 642. Base 744 may include or correspond to base 644. Interface 746 may include or correspond to interface 646. Interface 746 is configured to be coupled to tube 714.

Body 742 may define one or more cavities, such as a channel 750 (e.g., a first channel) into which one or more components may be positioned. For example, channel 750 may include a UV device (e.g., 118) or a light guide (e.g., 650). Channel 750 may include or correspond to cavity 504, and channel 750 may include interior volume 738. Additionally, body 742 may include one or more channels, such as one or more channels in fluid connection with first channel 750.

Further, body 742 may include one or channels or conduits, that extend from and/or are coupled to interface 146. For example, body 742 may include a conduit and a secondary channel (e.g., a reduced-pressure or exudate channel) that are in fluid communication with interior volume 738. To illustrate, the secondary channel may have an aperture defined by base 744, and which is positioned over manifold 734, to enable fluids and/or exudate to be drawn from target tissue 736. In some implementations, connector 730 may be positioned on manifold 734 such that a perimeter of the aperture (defined by base 744) is in direct contact with manifold 734. When the conduit and the second channel are in fluid communication with interior volume 738, connector 730 may operate to maintain fluid communication between interior volume 738 and device 710 via tube 714, and to prevent fluid communication between interior volume (e.g., a sealed therapeutic environment formed by dressing 716) and the ambient environment.

Tube 714 includes one or more lumens. For example, tube 714 may include a positive-pressure/fluid lumen (e.g., 621), a negative-pressure/fluid lumen, and one or more sense lumens. As shown, a first end of tube 714 is coupled to dressing 716 and a second end of tube 714 is coupled to device 710. In some implementations, the second end of tube 714 may include a therapy device connector configured to couple (e.g., mate) with device 710.

Device 710 includes a controller 760, one or more interfaces 762, one or more I/O devices 764, and one or more connectors, such as a representative connector 766. Device 710 further includes one or more conduits 768, a fluid chamber 770, a pressure sensor 774, one or more valves 776 (e.g., solenoid valves), and a positive-pressure source 778.

Connector 766, such as connector 138, is configured to be coupled to tube 714, such as the second end of tube 714. Connector 766 includes one or more port/interfaces, such as a first port/interface 780, a second port/interface 782, a third port/interface 784, a fourth port/interface 786. When connector 766 is coupled to tube 714, the positive-pressure/fluid lumen (e.g., 721) is in fluid communication with first port/interface 780, the negative-pressure/fluid lumen (e.g., 722) is in fluid communication with second port/interface 782, waveguide lumen (e.g., 724) is in fluid communication with third port/interface 784, and sense lumen (e.g., 726) is in fluid communication with fourth port/interface 786.

Each of first port/interface 782, second port/interface 782, third port/interface 784, and fourth port/interface 786 is coupled to one or more components of device 710 via one or more conduits (e.g., 768). For example, first port/interface 780 is coupled to positive-pressure source 778, second port/interface 782 is coupled through fluid chamber 770 (e.g., a canister or a liquid-collection cavity) to negative-pressure source 779, third port/interface 784 is coupled to a UV device 772, and fourth port/interface 786 is coupled to a pressure sensor 774. The pressure sensor 774 may be configured to generate data indicative of pressure within dressing 716. Although described as having a pressure sensor 774, in other implementations, device 710 may have no pressure sensors or more than one pressure sensor. Additionally, each of first port/interface 780, second port/interface 782, and fourth port/interface 786 is coupled to a corresponding valve (e.g., 776), such as a solenoid valve, which is configured to change pressure from dressing 716. First port/interface 780 is coupled to positive-pressure source 778 and a corresponding valve 776 via a conduit 768.

Positive-pressure source 778 is configured to provide positive-pressure to interior volume 738 of dressing 716 such that interior volume 738 is expanded, and/or positive-pressure is applied to at least target tissue 736. Positive-pressure source 778 may include a mechanically and/or electrically-powered device, such as a manually-actuated or manually-charged pump, an oxygen tank, an oxygen collector, a wall port, a micro-pump, a disc-pump, and/or the like, as illustrative, non-limiting examples.

In some implementations, device 710 further includes reduced-pressure source 779 that is configured to provide negative-pressure to interior volume 738 of dressing 716 such that interior volume 738 is reduced, and/or negative-pressure is applied to at least target tissue 736. Reduced-pressure source 779 may include a mechanically and/or electrically-powered device, such as a manually-actuated or manually-charged pump, a vacuum pump, an electrically-driven vacuum pump, a suction pump, a wall suction port, a micro-pump, a disc-pump, and/or the like, as illustrative, non-limiting examples. As illustrated in FIG. 7A, the positive-pressure source 778 and the reduced-pressure source 779 may operate in conjunction with each other and are applied to different portions of tissue site 720 via different lumens (e.g., 721, 722) of tube 714. In other implementations, the positive-pressure source 778 and the reduced-pressure source 779 share a lumen (e.g., 721 or 722) of tube 714 and the reduced-pressure source 779 operates in the alternative to the positive-pressure source 778 (e.g., operate in distinct cycles). For example, the reduced-pressure source 779 operates before or after the positive-pressure source 778 to remove exudate from tissue site 720.

Controller 760 includes a processor 790 coupled to a memory 792 (e.g., a computer-readable storage device). Memory 792, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. Memory 792 may be configured to store instructions 794, a pressure profile 796, and one or more thresholds 798. Instructions 794 may be configured to, when executed by the one or more processors 790, cause the processor(s) 790 to perform one or more operations.

Pressure profile 796 may include desired target pressures to be provided to a patient over a time period. In some implementations, the pressure profile 796 may include a set-up profile applying target pressures at the commencement of therapy treatments and a maintenance profile for applying target pressure during therapy. One or more thresholds 798 may include one or more one or more pressure thresholds, one or more time thresholds, one or more other thresholds, or a combination thereof.

Processor 790 may include a microcontroller/microprocessor, a central processing unit (CPU), a field-programmable gate array (FPGA) device, an application-specific integrated circuits (ASIC), another hardware device, a firmware device, or any combination thereof. Processor 790 may be configured to execute instructions 794, execute and/or operate according to pressure profile 796, and/process sensor data generate by pressure sensor 774. For example, processor 790 may be configured to process sensor data (e.g., pressure signals) received by one or more pressure sensors (e.g., 774) and/or monitor the sensor data. Additionally, or alternatively, processor 790 may be configured to issue one or more alerts according to a pre-determined pressure therapy (e.g., pressure profile 796) for a patient and/or based on one or more thresholds 798. In some implementations, the one or more alerts may be in the form of a visual alert (e.g., a light indicator), a tactile alert, an audible alert, a message presented via a display, or a message transmitted to another device. In the event that processor 790 determines that pressure profile 796 is being implemented, processor 790 may provide an indication that the sensor data (e.g., the monitored pressure at dressing 716) is following pressure profile 796. For example, processor 790 may initiate a visual indication (e.g., a light indicator), a tactile indication, an audible indication, a message presented via a display, or a message transmitted to another device.

The one or more interfaces 762 may include a wired interface, a wireless interface, or both. In some implementation, the one or more interfaces 762 may include a network interface and/or a device interface configured to be communicatively coupled to one or more other devices. For example, interfaces 762 may include a transmitter, a receiver, or a combination thereof (e.g., a transceiver), and may enable wired communication, wireless communication, or a combination thereof. Additionally, or alternatively, the one or more interfaces 762 may include serial interfaces (e.g., universal serial bus (USB) interfaces or Institute of Electrical and Electronics Engineers (IEEE) 1394 interfaces), parallel interfaces, display adapters, audio adapters, and other interfaces. The one or more I/O devices 764 may include a mouse, a keyboard, pointing devices, a display device, the camera, speakers, microphones, touch screens, other I/O devices, or a combination thereof. Processor 790 may configured to send and/or receive data via the interface (s) 762 and/or the I/O device(s) 764.

During operation, dressing 716 is coupled to tissue site 720 so as to cover target tissue 736. Additionally, dressing 716 is coupled to device 710 via tube 714. In some implementations, processor 790 receives an input via I/O device 764, such as a touchscreen, to select a pressure profile (e.g., 796) of multiple pressure profiles stored at memory 792, to initiate positive-pressure therapy, or both. Alternatively, the input may indicate a value of a positive-pressure to be provided and/or maintained. Responsive to the input, controller 760 (e.g., processor 790) generates one or more commands to initiate operations of one or more components of device 710. For example, processor 790 may access pressure profile 796 (e.g., a set-up profile or a maintenance profile). Additionally, or alternatively, processor 790 may activate and/or regulate positive-pressure source 778, one or more valves 776, or both. In some implementations, processor 790 may control operation of positive-pressure source 778, one or more valves 776 based on at least in part on the input (e.g., the pressure profile 796 selection or the value of the positive-pressure).

Responsive to one or more signals (e.g., commands) from processor 790, positive-pressure source 778 may apply positive-pressure to dressing 716. For example, positive-pressure developed by positive-pressure source 778 may be delivered through tube 714 to connector 730 of dressing 716. Accordingly, the positive-pressure source 778 can increase a pressure in interior volume 738. Internal volume (e.g., a sealed therapeutic environment) and/or target tissue 736 may be isolated from an external environment (associated with an ambient pressure).

As positive-pressure is provided via pressure/fluid lumen (e.g., 121), pressure at dressing 716 may be communicated to pressure sensor 774 via sense lumen (e.g., 726). The pressure communicated by via sense lumen (e.g., 726) may be representative of the pressure at the target tissue 736. Pressure sensor 774 is configured to generate sensor data that is communicated to controller 760 (e.g., processor 790). The sensor data provided to controller 760 enables device 710 to track treatment provided to target tissue 736 via dressing 716. Based on the sensor data, controller 760 (e.g., processor 790) may initiate operation of one or more valves (e.g., 776) between an open position and a closed position.

For example, processor 790 may be configured to adjust a particular valve in response to a comparison of the sensor data (indicating that a pressure within the interior volume (e.g., 738) to a threshold (e.g., 798).

In some implementations, processor 790 is configured to control positive-pressure source 778 (e.g., a positive-pressure source device) and/or one or more valves 776 based at least in part on the sensor data. For example, processor 790 may be configured to deactivate positive-pressure source 778 in response to a determination that the sensor data indicates that a pressure within the interior volume (e.g., 738) is less than a first threshold (e.g., a first threshold pressure value). In some implementations, processor 790 is configured to operate at least one valve (e.g., 776) towards the open position upon or after deactivation of positive-pressure source 778. To illustrate, the at least one valve may include the valve coupled to positive-pressure source 778, and/or the valve coupled to pressure sensor 774. As another example, processor 790 may be configured to activate positive-pressure source 778 in response to a determination that the sensor data indicate that a pressure within the interior volume (e.g., 738) is greater than or equal to a second threshold (e.g., a second threshold pressure value). Activation of positive-pressure source 778 may increase pressure within the interior volume (e.g., 738). In some implementations, processor 790 is configured to operate at least one valve (e.g., 776) towards the closed position upon or after activation of positive-pressure source 778. The first threshold and the second threshold may have the same value. Alternatively, the first threshold and the second threshold may have different values (e.g., the second threshold may be greater than the first threshold).

Controller 760 may operate valve 776 coupled to pressure sensor 774 based on sensor data received from pressure sensor 774 and/or based on a set of one or more thresholds (e.g., 798). Additionally, or alternatively, in other implementations, controller 760 may operate one or more of the valves based on an average of sensor data of two or more pressure sensors. For example, controller 760 may control one or more valves, such as the valve coupled to positive-pressure source 778 based on an average of the sensor data (received from pressure sensor 774 and another sensor) and the set of one or more thresholds.

Positive-pressure provided by positive-pressure source 778 via tube 714 can cause pressurized fluid (e.g., oxygen or medication) to be provided to target tissue 736 (e.g., tissue site 720) via tube 714 (e.g., positive-pressure/fluid lumen) and first port/interface 780. In some implementations, device 710 may include a sensor and/or regulator (not shown) coupled to controller 760 (e.g. processor 790) and configured to monitor a pressure of the positive-pressure source 778 or the corresponding conduit 768 thereof. For example, processor 790 may receive sensor data from the sensor that indicates a pressure level of the regulator and may operate valve 776 to control a pressure and/or volume of positive-pressure source 778. Once a desired pressure of fluid is achieved, the pressurized fluid (e.g., oxygen) may be provided to target tissue 736.

Reduced-pressure provided by reduced-pressure source 779 via tube 714 can cause exudate, fluid, and/or another material to be drawn (e.g., removed) from target tissue 736 (e.g., tissue site 720) via tube 714 (e.g., reduced-pressure/fluid lumen) and second port/interface 782. Exudate, fluid, and/or another material removed via second port/interface 782 may be collected in fluid chamber 770 (e.g., a canister, such as canister 112, 612) for disposal. In some implementations, device 710 may include a sensor (not shown) coupled to controller 760 (e.g. processor 790) and configured to monitor a volume of fluid chamber 770. For example, processor 790 may receive sensor data from the sensor that indicates a fill level of fluid chamber 770. In response to a determination by processor 790 that the fill level is greater than or equal to a threshold (e.g., a threshold fill level value), processor 790 is configured to deactivation of reduced-pressure source 779, operate at least one valve (e.g., 776) towards the open position, or both. Additionally, or alternatively, based on a determination by processor 790 that the fill level is greater than or equal to a threshold, processor 790 may initiate a notification (e.g., an alarm), such as a message via a display, an audio and/or visual notification, transmit a data message to another device, or a combination thereof.

When fluid chamber 770 is empty, as in positive-pressure implementations, or when fluid chamber 770 is full, as in reduced-pressure implementations, operation of device 710 may be paused or stopped to perform a partial disconnect (e.g., replace fluid chamber 770 with a new fluid chamber 77) or a full disconnect.

Alternatively, controller 760 can operate a timer to control a duration of operation of therapy or an expiration time of therapy, i.e., an activation duration for device 710. Controller 760 may output an audio and/or visual notification to indicate replacement of a component (e.g., fluid chamber 770 or dressing 716) or completion of a therapy treatment or session.

Responsive to a determination regarding fluid chamber 770 fill level or timer, controller 760 may deactivate device 710 and activate UV device 772. Responsive to activation, UV device 772 emits UV light via conduit 768 to tube 714 via port/interface 748. Tube 714 (e.g., one or more lumens thereof, such as lumen 724) transports the emitted UV light to connection points of system 700. For example, lumen 724 is a dedicated waveguide lumen with high reflectivity and/or includes a sheath or coating to increase reflectively and reduce transmission of UV light through walls of lumen 724 to other lumens and outside tube 714. As another example, walls of tube 714 reflect UV light to transport the UV light along a length of tube 714. An illustrative light propagation path 773 is depicted in FIG. 7 to illustrate one example path of the UV light emitted from UV device 772 propagating through conduit 768, port/interface 748, tubes 714 (e.g., reflecting off walls thereof), and connector 730 to dressing 716, where the UV light can be transported or dispersed to adhesive 737 by dressing 716, as described with reference to FIGS. 1, 5, and 6A.

In other implementations, UV device 772 emits light into fluid chamber 770 and, via fluid chamber 770 and/or conduit 768 associated with fluid chamber 770, into port/interface 782. In such implementations, UV light can further activate LSA of a connection point between fluid chamber 770 and device 710.

Additionally, or alternatively, controller 760 activates and/or controls UV device 772 responsive to receiving a wireless communication via interface(s) 762 (e.g., a wireless interface). To illustrate, a remote control or mobile device transmits a code or password (i.e., data indicating a code or password) to controller 760. Processor 790 determines whether a received code or password matches a code or password stored in memory 792. Responsive to determining a match and authenticating the code or password, controller 760 sends an activation signal to UV device 772 to cause UV device 772 to emit light.

Additionally, or alternatively, controller 760 activates and/or controls UV device 772 responsive to receiving an input via I/O device(s) 764. In some implementations, the input corresponds to a code or password. In other implementations, the input corresponds to an activation signal from an activation button. In some implementations, controller 760 can receive inputs (i.e., data indicating) to set a timer (duration of device 710 or UV device 772), delay time, activation time, etc., via interface(s) 762 (e.g., a wireless interface), I/O device(s) 764, or a combination thereof. In some implementations, controller 760 adjusts a power or intensity of UV device 772 to control how far the emitted UV light travels in system 700. For example, at a high power setting, UV light can be transported to dressing 716 in sufficient power to transition LSA thereof, and, at a low power setting (relative to the high power setting), UV light can be transported to tube 714 in sufficient power to transition LSA thereof. The high power setting may correspond to a maximum or design setting for power or intensity such that the UV light can be transported through multiple components of the system 700. The low power setting may correspond to a design setting for power or intensity such that the UV light can be transported through one component and/or through less than all components of the system 700, such as a portion of light propagation path 773.

In some implementations, one or more lumens of tube 714 may end at or include transmission elements associated with connection points and controller 760 is configured to control which lumens of tube 714 receive light from UV device 772. Thus, controller 760 may selectively supply light to selected connection points, such as connection points 160-168 of FIG. 1 or other connections points described herein. For example, controller 760 receives data indicating one or more connection points to be disconnected via interface(s) 762 (e.g., a wireless interface), I/O device(s) 764, or a combination thereof. Responsive to receiving the selected connection point or points, controller 760 sends control signals to UV device 772, valves associated with conduits 768, light guide elements, or a combination thereof. For example, controller 760 may open and close valves in one or more conduits 768 to allow or block one or more lumens corresponding to the one or more conduits 768 from receiving light. As another example, controller 760 sends control signals to UV device 772, and UV device 772 activates one or more LEDs thereof associated with lumens corresponding to the selected connection point or points. To illustrate, UV device 772 provides UV light a first lumen of tube 714 which has a transmission element at an in-line connector connection point, such as connection point 162, and UV device 772 does not provide light to other lumens of tube 714 which have transmission elements at or near other connection points of system 700.

Thus, FIG. 7A describes system 700 for controlling the application of light to connection points of system 700 to activate LSA. System 700 may advantageously include UV device 772 configured to generate UV light and one or more components to transport the UV light to LSA of connection points of system 700 to activate the LSA. For example, applying UV light to the LSA transitions the LSA from the high tack state to the low tack state to enable disconnection of the connection points. Thus, system 700 provides secure single-use connections and hinders or prevents reuse of single-use components to reduce infection and contamination. Additionally, system 700 provides easy assembly and disconnection with a low disconnection force enabling the young, elderly, and sick to easily connect and disconnect components of system 700. Furthermore, system 700 may advantageously include light guide, cover films, port/windows or other components described herein to further enable protection of LSA and selective activation of connection points.

Figure 8:
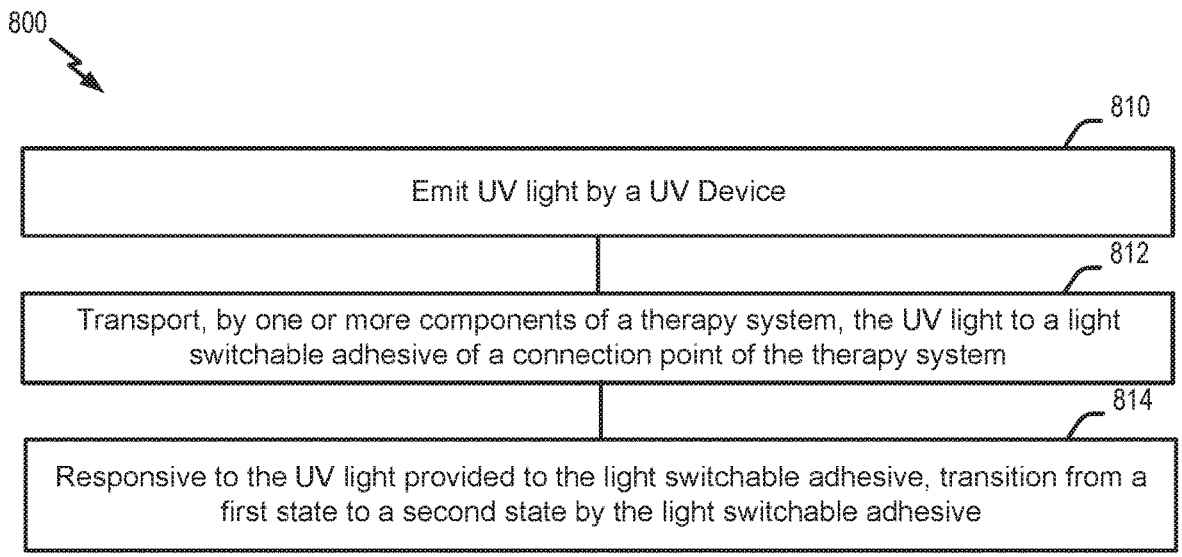
FIG. 8 is a flowchart illustrating an example of a method of disconnecting a connection point of a therapy system.

FIG. 8 illustrates a method 800 of disconnecting a connection point of a therapy system. The method 800 may be performed at, by, or with system 100 (e.g., one or more components thereof), a system that includes one or more of a connector (130, 150, 152, 154, 254, 354, 454, 630, 638, 730), a tube (e.g., 114, 614, 714), or a light source (e.g., UV device 118, 518), the system 600 (e.g., one or more components thereof), or the system 700 (e.g., one or more components thereof).

Method 800 includes emitting UV light by a UV Device, at 810. The UV Device may include or correspond to UV Device 118, second light device 518, or UV Device 772.

Method 800 further includes, transporting, by one or more components of a therapy system, the UV light to a light switchable adhesive of a connection point of the therapy system, at 812. For example, the therapy system may include or correspond to system 100, system 600, or system 700, and the one or more components thereof may include or correspond to components 110, 112, 114, 116, 130, 150, 152, 154, 254, 354, 454, 504, 512, 522, 610, 612, 614, 616, 630, 632 642, 644, 650, 710, 712, 714, 716, 730, 732, 768, 784 or a combination thereof. The light switchable adhesive may include or correspond to LSA 140, two-part LSA 140 (e.g., part 440, part 440), second type LSA 440, or a combination thereof. The connection point may include or correspond to one of connection points 162-168, 202-206, 302-306, 402, 404, one of the connection points of FIG. 5, one of the connection points of FIG. 6A, or one of the connection points of FIG. 7A.

Method 800 further includes, responsive to the UV light provided to the light switchable adhesive, transition from a first state to a second state by the light switchable adhesive, at 814. For example, the first state may include or correspond to a state with a first peel strength, and the second state may include or corresponds to a state with a second peel strength that is less than the first peel strength. To illustrate, photo initiators of LSA 140 cross-link with each other or free radicals to reduce peel strength and tackiness of LSA 140.

Thus, method 800 describes operation of disconnecting a connection point of a therapy system by applying light to a light switchable adhesive of the connection point. Therefore, a patient or care provider can easily disconnect the components and is hindered or restricted from reusing the components which form the connection point. Accordingly, the single-use components may enable sterile, efficient, and safe use of the therapy system.

Figure 9:
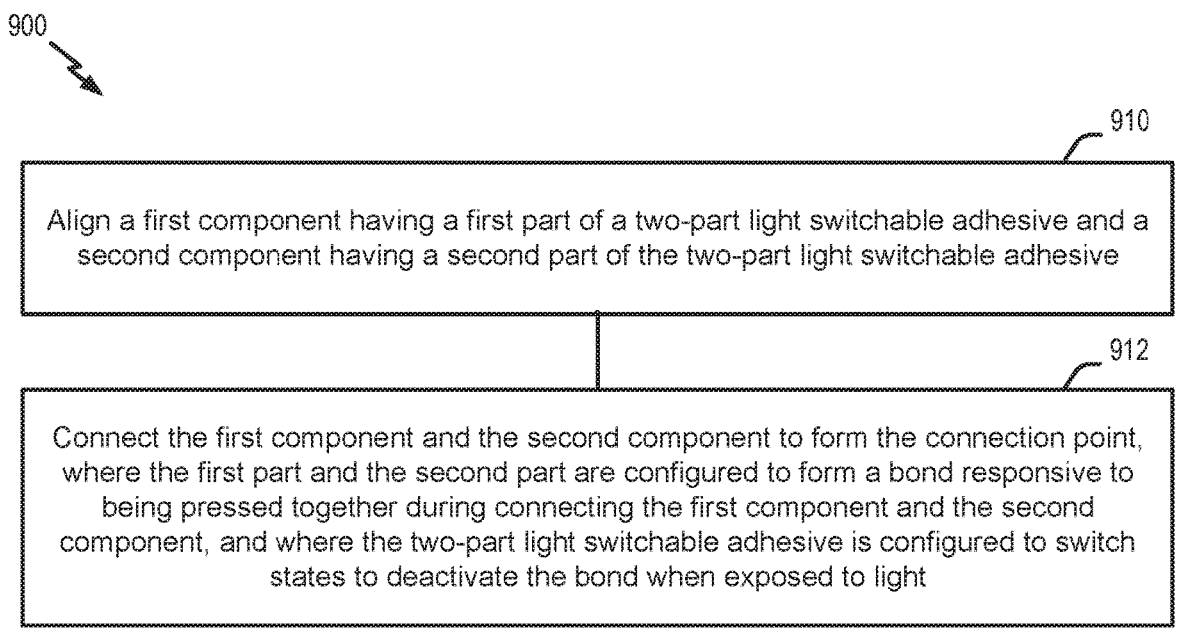
FIG. 9 is a flowchart illustrating an example of a method of forming a connection point of a therapy system.

FIG. 9 illustrates a method 900 of forming a connection point of a therapy system. The method 900 may be performed at or with system 100 (e.g., one or more components thereof), a system that includes a connector (e.g., 130, 150, 152, 154, 254, 354, 454, 630, 730) or a tube (e.g., 114, 614, 714), the system 600 (e.g., one or more components thereof), or the system 700 (e.g., one or more components thereof).

Method 900 includes aligning a first component having a first part of a two-part light switchable adhesive and a second component having a second part of the two-part light switchable adhesive, at 910. For example, the first part may include or correspond to first part 440 of LSA 140, and the second part may include or correspond to second part 442 of LSA 140. The first component and the second component may include or correspond to a connector (e.g., 130, 150, 152, 154, 254, 354, 454, 630, 730) a tube (e.g., 114, 614, 714), a dressing (e.g., 116, 616, 716), a canister (e.g., 112,

612, 770), a therapy device (e.g., 110, 610, 710), or a patient (e.g., 120, 620, 720). To illustrate, a pattern 432 of first part 440 on a first component and a corresponding pattern 423 of second part 442 on a second component are aligned. In a particular implementation a mechanical guide feature is used to align the components, such as guide pin 222 and a slot 224. To illustrate, aligning the guide pin 222 of the first component and the slot 224 of the second component aligns the patterns 432 of the first and second part 440, 442 such that the first and second part 440, 442 come into contact and form a bond when pushed together. Additionally or alternatively, aligning lumens of the components may align the first and second part 440, 442 or aligning the mechanical features may align the lumens of the components.

Method 900 further includes connecting the first component and the second component to form the connection point, at 912. The first part and the second part are configured to form a bond responsive to being pressed together during connecting the first component and the second component, and the two-part light switchable adhesive is configured to switch states to deactivate the bond when exposed to light. For example, the first component is inserted into the second component. To illustrate, a mating portion (312) or interface end (212) of the first component is inserted into a recess (214) or a port in or defined by the second component. Thus, method 900 describes operation of forming a connection point with a two-part LSA and enables formation of a light switchable bond between designed components and in a designed orientation. Therefore, a misconnection of components or a misalignment of components will not form a bond and will not prevent use of the component(s) after a misconnection or a misalignment.

It is noted that one or more operations described with reference to one of the methods of FIGS. 8-9 may be combined with one or more operations of another of FIGS. 8-9. For example, one or more operations of method 800 may be combined with one or more operations of method 900. Additionally, or alternatively, one or more operations described above with reference to FIGS. 1A, 1B, 2A-2D, 3A-3D, 4A-4C, 5, 6A, 6B, 7A, and 7B may be combine with one or more operations of FIG. 8, FIG. 9, or a combination of FIGS. 8 and 9.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A therapy system comprising:
   a connection point including a connector having a light switchable adhesive provided on a mating portion of the connector; and
   a UV device configured to provide light to the light switchable adhesive via one or more components of the therapy system;
   the light switchable adhesive being configured to switch states based on a first light, and further comprising a second light switchable adhesive, the second light switchable adhesive configured to switch states based on a second light, wherein the second light corresponds to a different spectrum than the first light.

2. The therapy system of claim 1, wherein the connection point comprises a connection point between a therapy device and a canister, between the canister and a set of tubes, within the set of tubes, or between the set of tubes and a dressing.

3. The therapy system of claim 1, further comprising a therapy device and a dressing in fluid communication with the therapy device.

* * * * *